(12) United States Patent
Chu et al.

(10) Patent No.: US 9,936,964 B2
(45) Date of Patent: Apr. 10, 2018

(54) RETRIEVAL DEVICES AND RELATED METHODS OF USE

(71) Applicant: Boston Scientific Scimed, Inc., Maple Grove, MN (US)

(72) Inventors: Michael S. H. Chu, Brookline, MA (US); Kimberly DeGraaf, Holden, MA (US); Peter J. Pereira, Mendon, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 237 days.

(21) Appl. No.: 14/711,348

(22) Filed: May 13, 2015

(65) Prior Publication Data
US 2015/0327878 A1 Nov. 19, 2015

Related U.S. Application Data

(60) Provisional application No. 61/993,678, filed on May 15, 2014, provisional application No. 61/993,825, filed on May 15, 2014.

(51) Int. Cl.
*A61B 17/22* (2006.01)
*A61B 90/00* (2016.01)
(Continued)

(52) U.S. Cl.
CPC ...... *A61B 17/22031* (2013.01); *A61B 17/221* (2013.01); *A61B 90/03* (2016.02);
(Continued)

(58) Field of Classification Search
CPC ............ A61B 17/221; A61B 17/22031; A61B 2017/2212
See application file for complete search history.

(56) References Cited

U.S. PATENT DOCUMENTS 4,198,960 A * 4/1980 Utsugi ................. A61B 1/0125
600/104
4,222,380 A * 9/1980 Terayama ............. A61M 5/425
600/104

(Continued)

FOREIGN PATENT DOCUMENTS

WO       WO 98/48710 A1    11/1998
WO       WO 99/16363 A1     4/1999

OTHER PUBLICATIONS

International Search Report and Written Opinion in PCT/US2015/030781, dated Jul. 20, 2015 (13 pages).

*Primary Examiner* — Alexander Orkin
(74) *Attorney, Agent, or Firm* — Bookoff McAndrews, PLLC

(57) ABSTRACT

A retrieval device may include a sheath including a distal end and a proximal end, and an end effector at the distal end. At least a portion of the end effector may be movable relative to the sheath between extended and retracted states. The end effector may include a support member extending from the distal end of the sheath, and a movable member extending from the distal end of the support member. The device may include a handle assembly at the proximal end of the sheath, having an actuation member for transitioning the end effector between the extended and retracted states. The device may include a biasing member coupled to at least one of the actuation member and the sheath that may control a force, exerted by one of the movable members and the support member on the other, generated by relative movement between the movable and support members.

20 Claims, 17 Drawing Sheets

(51) Int. Cl.
    *A61B 17/221*    (2006.01)
    *A61B 17/30*     (2006.01)

(52) U.S. Cl.
    CPC ............... *A61B 2017/2212* (2013.01); *A61B 2017/2215* (2013.01); *A61B 2017/22035* (2013.01); *A61B 2017/305* (2013.01)

(56) References Cited

U.S. PATENT DOCUMENTS

| | | | |
|---|---|---|---|
| 5,501,692 A * | 3/1996 | Riza | A61B 17/0469 112/169 |
| 5,906,622 A | 5/1999 | Lippitt et al. | |
| 5,924,175 A | 7/1999 | Lippitt et al. | |
| 6,146,396 A * | 11/2000 | Konya | A61B 17/221 606/159 |
| 6,193,672 B1 | 2/2001 | Clement | |
| 6,454,775 B1 * | 9/2002 | Demarais | A61B 17/320725 606/128 |
| 6,458,145 B1 | 10/2002 | Ravenscroft et al. | |
| 6,626,915 B2 | 9/2003 | Leveillee | |
| 6,652,537 B2 * | 11/2003 | Mercereau | A61B 17/221 606/113 |
| 6,743,228 B2 * | 6/2004 | Lee | A61B 8/0825 606/113 |
| 7,041,108 B2 | 5/2006 | Lippitt et al. | |
| 7,210,210 B2 | 5/2007 | Lippitt et al. | |
| 2001/0047169 A1 | 11/2001 | McGuckin et al. | |
| 2003/0109888 A1 * | 6/2003 | Mercereau | A61B 17/221 606/127 |
| 2004/0215212 A1 * | 10/2004 | Teague | A61B 17/221 606/127 |
| 2007/0106304 A1 * | 5/2007 | Hammack | A61B 17/221 606/113 |

* cited by examiner

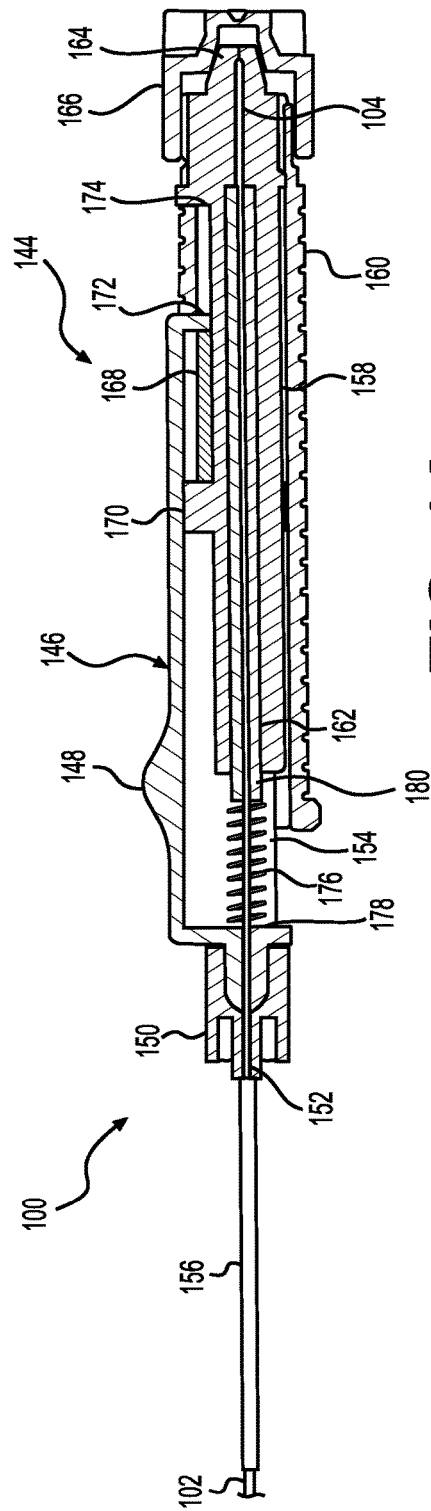
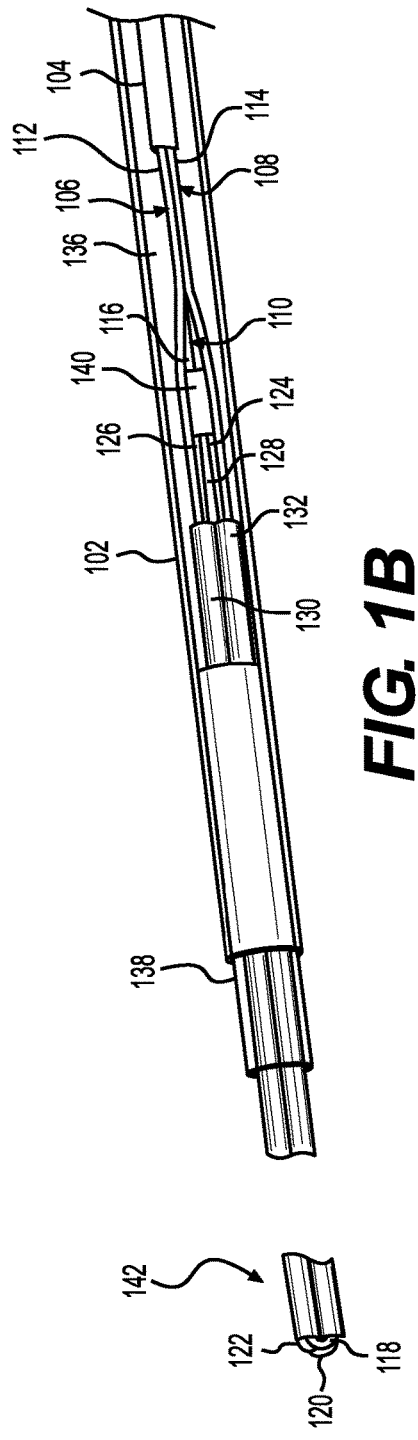
FIG. 1A
FIG. 1B

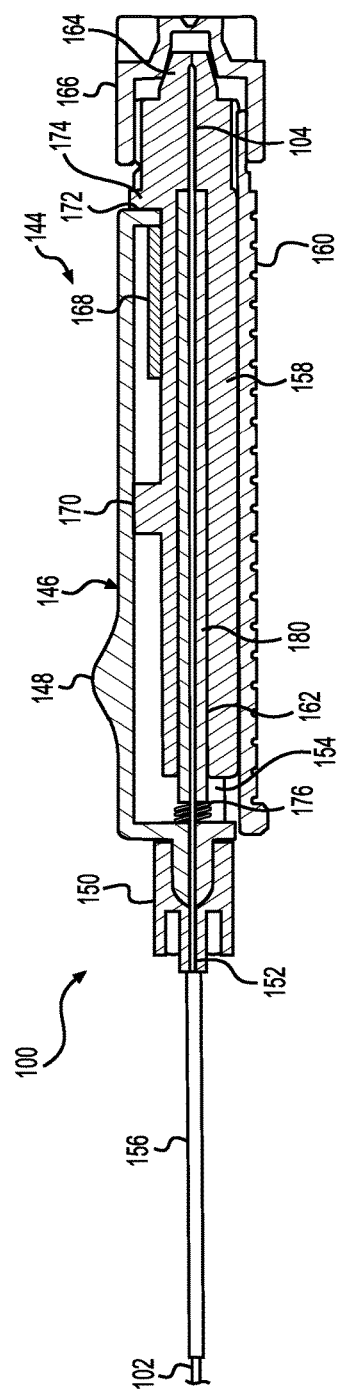
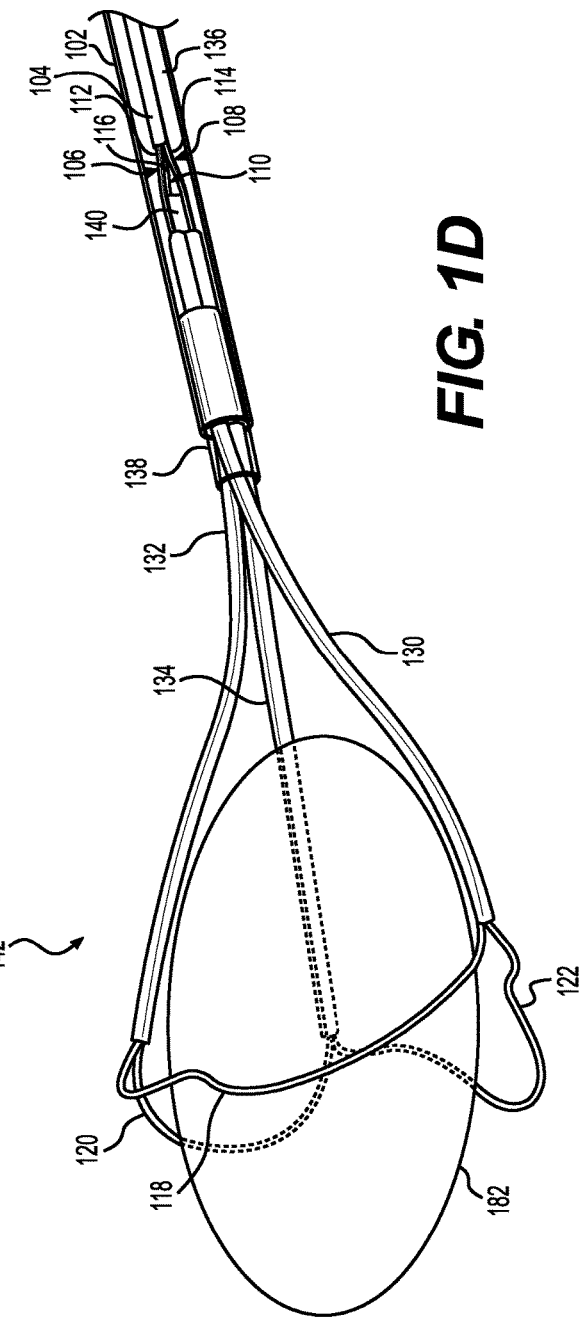
FIG. 1C
FIG. 1D

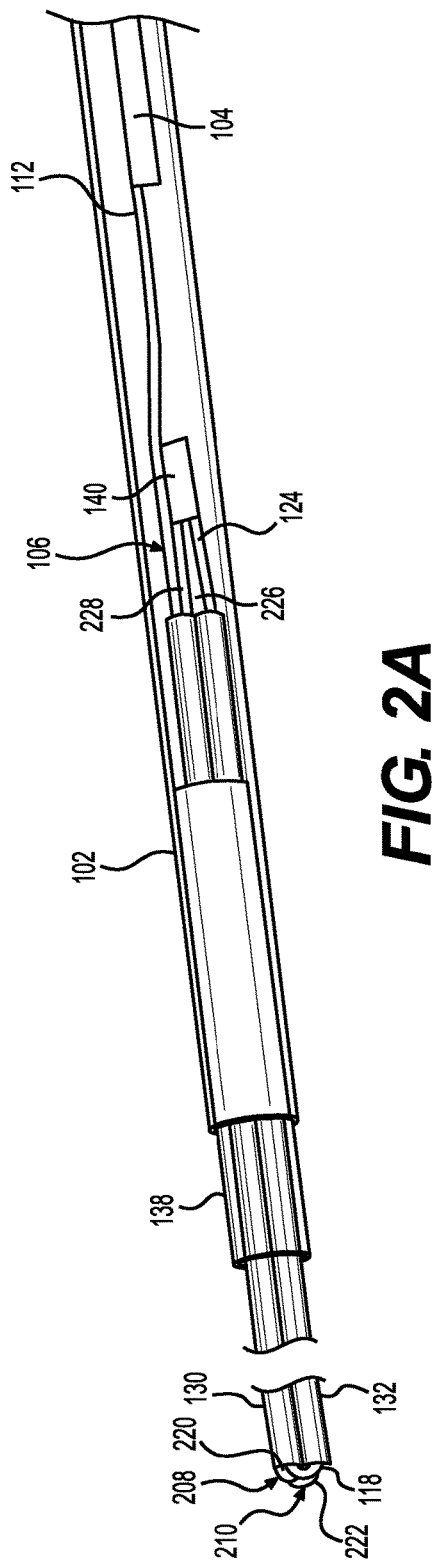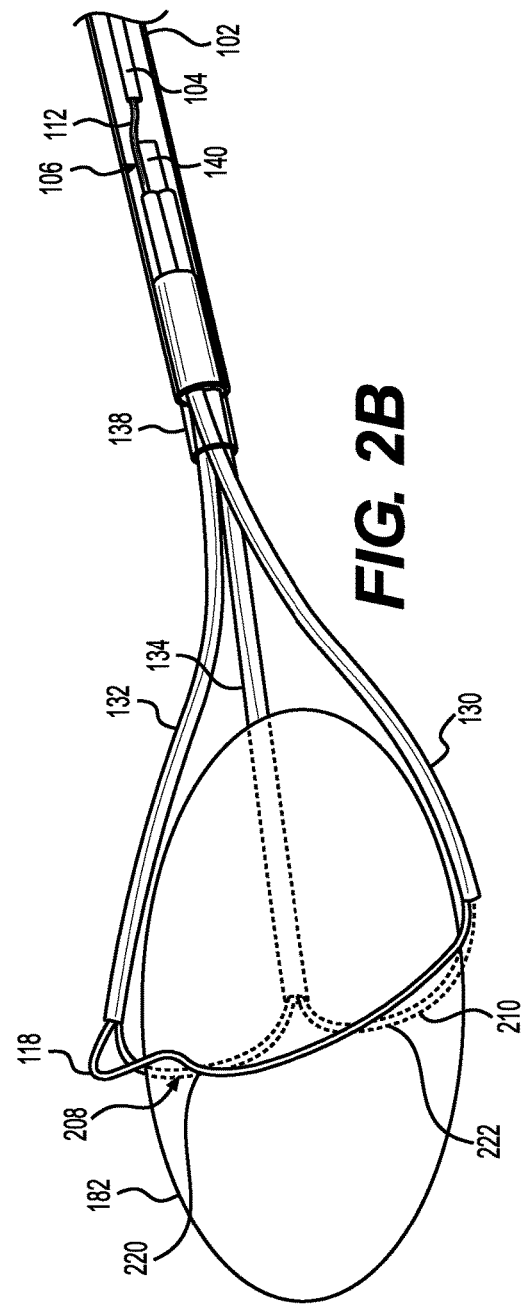
FIG. 2A
FIG. 2B

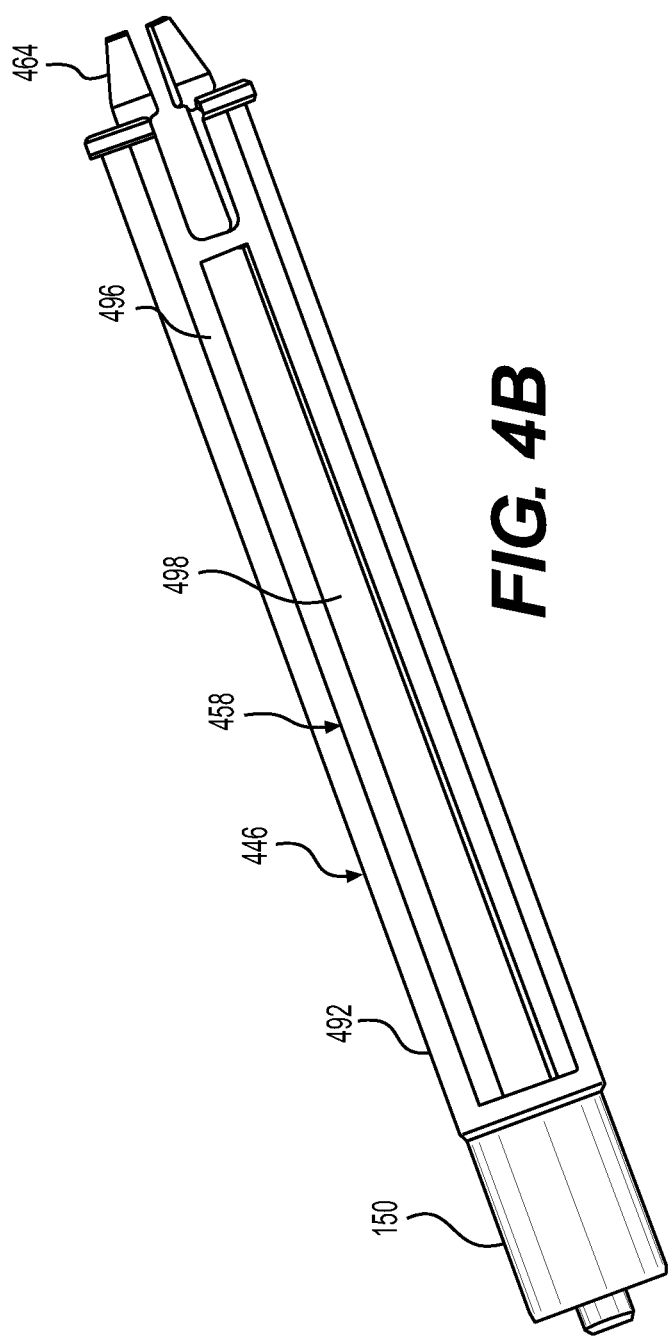

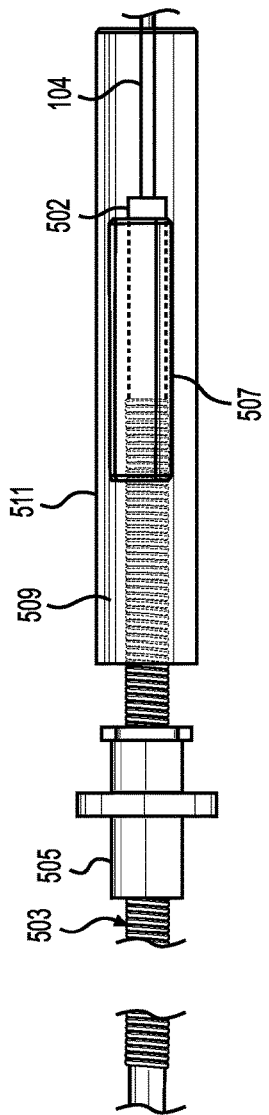
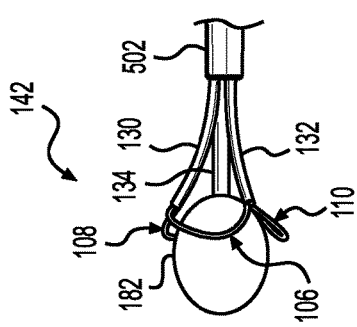
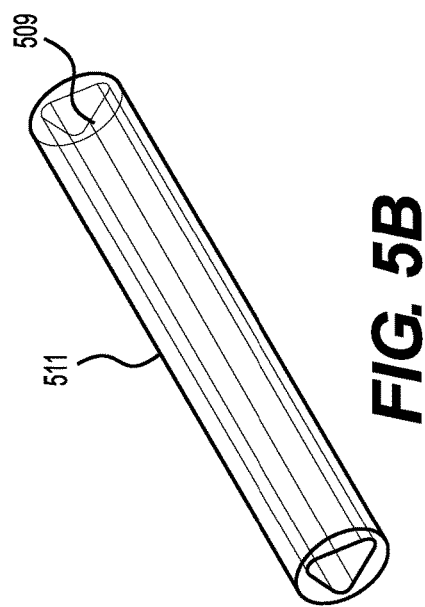
FIG. 5A
FIG. 5B

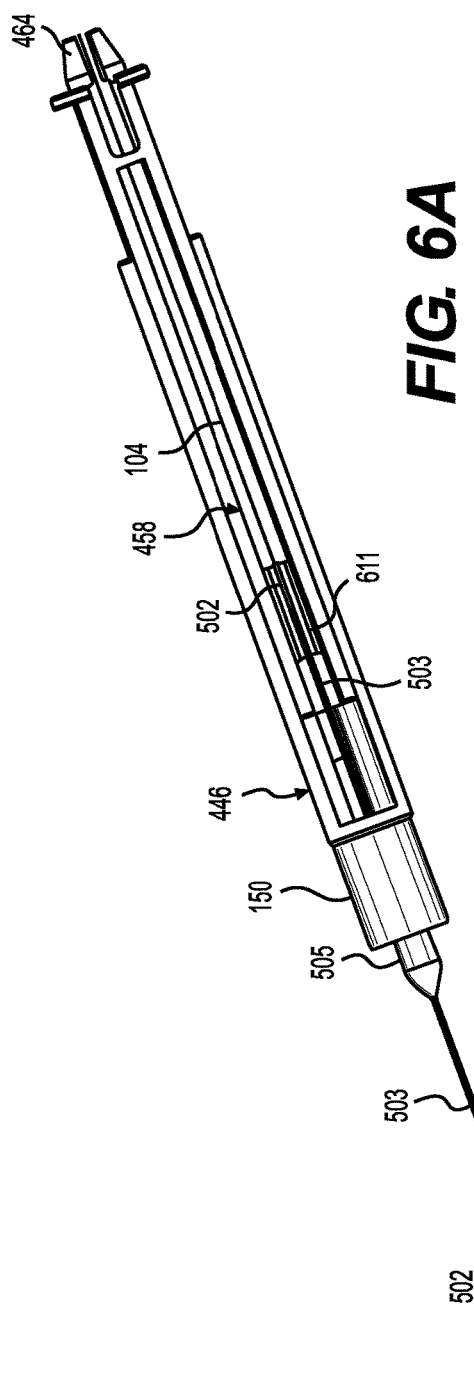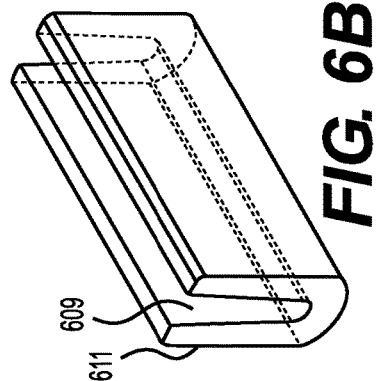

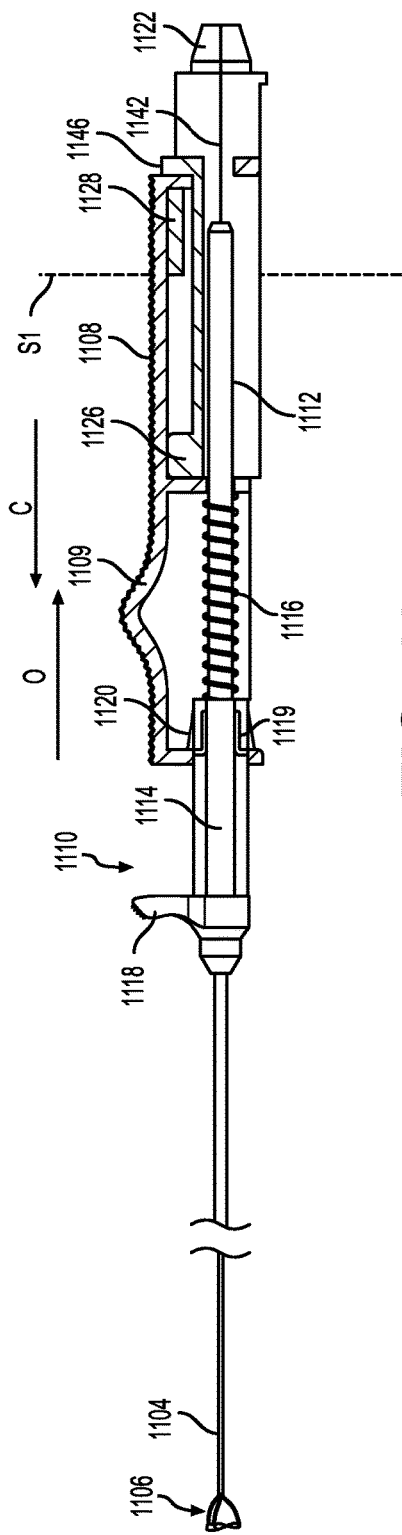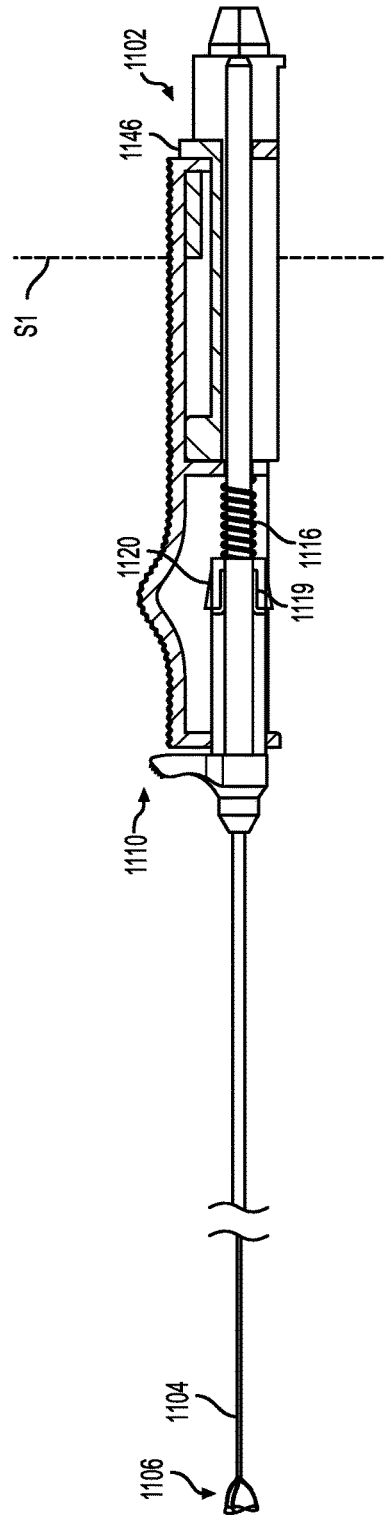
FIG. 13
FIG. 14

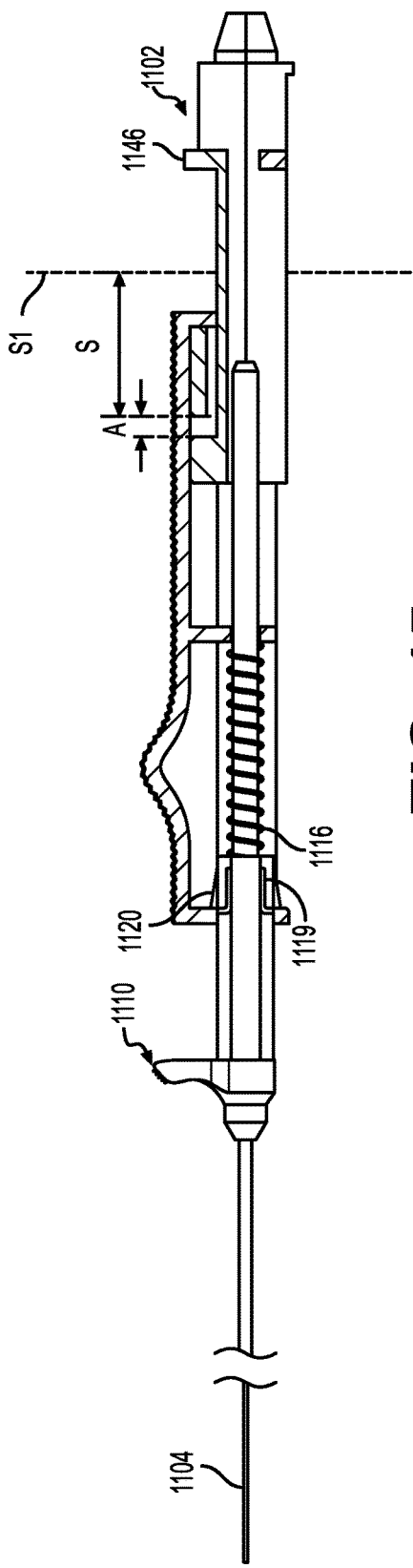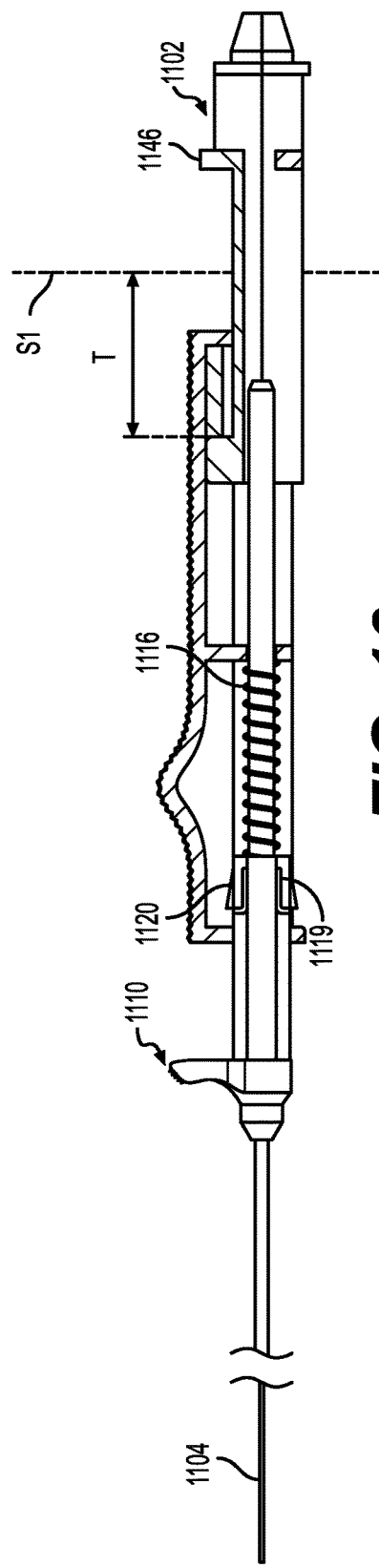

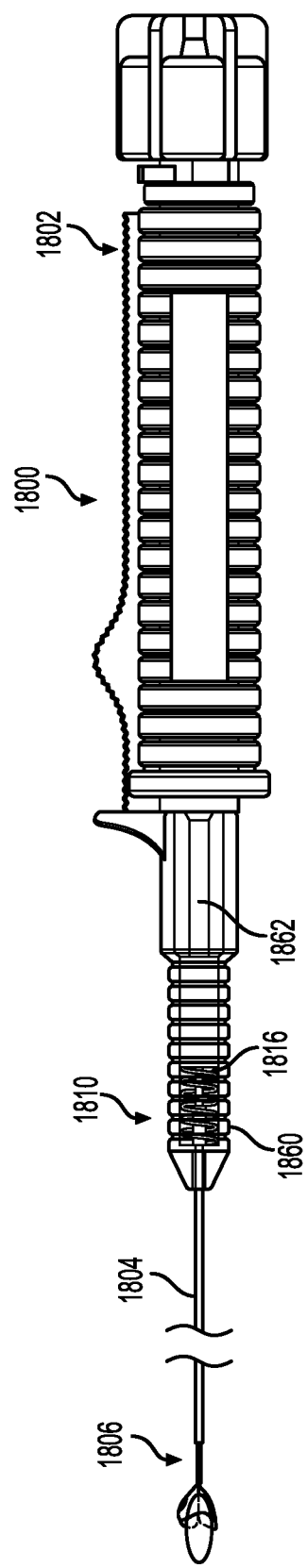

RETRIEVAL DEVICES AND RELATED METHODS OF USE

CROSS-REFERENCE TO RELATED APPLICATIONS

The application claims the benefits of priority from U.S. Provisional Application No. 61/993,678, filed on May 15, 2014, and U.S. Provisional Application No. 61/993,825, filed on May 15, 2014, each of which is incorporated by reference herein in its entirety.

TECHNICAL FIELD

Various aspects of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Retrieval devices are also used in lithotripsy and ureteroscopy procedures to treat urinary calculi (e.g., kidney stones) in the ureter of a patient.

Retrieval devices may include end effectors for manipulating objects. An exemplary end effector may have a plurality of arms that support a front loop that forms when the end effector is opened. A user may use the arms and front loop to capture objects and/or release captured objects. The user's ability to capture and/or release an object may depend on factors, including, for example, the ability of the arms and front loop to exert a grasping force on the object, the size of gaps or openings between the arms, and/or the size of the front loop. Some retrieval devices may be limited in their ability to retrieve objects due, for example, to the size of the end effector in its extended state (e.g., the end effector being too large or too small), and may be prone to breakage and/or require assistance from additional devices to remove large objects that cannot otherwise be released from the end effector. Thus, there remains a need for retrieval devices with improved capabilities.

The exemplary features of the present disclosure are directed to improvements in retrieval devices and related methods of use.

SUMMARY

Aspects of the present disclosure relate to, among other things, retrieval devices and related systems and methods. Each of the aspects disclosed herein may include one or more of the features described in connection with any of the other disclosed aspects.

According to aspects of the present disclosure, a device may include a sheath including a distal end and a proximal end. The device may also include an end effector at the distal end of the sheath. At least a portion of the end effector may be movable relative to the sheath between an extended state and a retracted state. The end effector may include a support member extending from the distal end of the sheath, and a movable member extending from the distal end of the support member. The device may also include a handle assembly at the proximal end of the sheath. The handle assembly may include an actuation member for transitioning the end effector between the extended state and the retracted state. The device may also include a biasing member coupled to at least one of the actuation member and the sheath. The biasing member may control a force exerted by one of the movable member and the support member on the other of the movable member and the support member. The force may be generated by relative movement between the movable member and the support member.

In addition or alternatively, the device may include one or more of the features below. The biasing member may be movable between a rest state and a biasing state, the biasing member being compressed or elongated from the rest state to the biasing state. The biasing member may move to the biasing state as the end effector transitions to the extended state. The biasing member may move from the biasing state to the rest state to transition the end effector to the retracted state with a predetermined force. The biasing member may move to the biasing state when the force between the movable member and the support member is outside of a predetermined range. Movement of the biasing member to the biasing state may be caused by relative movement between the actuation member and the sheath. The handle assembly may include a handle body slidably coupled to the actuation member. The biasing member may surround at least a portion of the sheath. The biasing member may have a proximal end fixedly coupled to the sheath, and a distal end movable relative to the sheath. The biasing member may be fixedly coupled to the actuation member. The biasing member may have a proximal end fixedly coupled to the sheath, and a distal end fixedly coupled to the sheath. The sheath may include at least two sections having different degrees of stiffness. The biasing member may overlap at least a portion of each of the two sections. A connector may connect the handle assembly to the proximal end of the sheath. The connector may include a port in fluid communication with a lumen of the sheath for injecting a fluid into the lumen of the sheath.

According to aspects of the present disclosure, a method for operating a device including a sheath, an end effector, a handle assembly, and a biasing member, may include transitioning the end effector from an extended state to a retracted state. The end effector may be at the distal end of the sheath, and the end effector may include a support member extending from the distal end of the sheath, and a movable member extending from the distal end of the support member. The method may also include actuating an actuation member on the handle assembly at the proximal end of the sheath to transition the end effector from the extended state to the retracted state. The method may also include controlling a force, exerted on one of the movable member and the support member by the other of the movable member and the support member, with the biasing member. The force may be generated by moving one of the movable member and the support member relative to the other of the movable member and the support member. The biasing member may be coupled to at least one of the actuation member and the sheath.

In addition or alternatively, the method may include controlling the force with the biasing member. Controlling the force may include deforming the biasing member when the force exceeds a predetermined range.

According to aspects of the present disclosure, a device may include a sheath including a distal end and a proximal end. The device may also include an end effector at the distal end of the sheath. The end effector may include a plurality of support arms and a plurality of movable members extending from the support arms. The end effector may be movable between an extended state and a retracted state via relative movement between the plurality of support arms and the plurality of movable members. The device may also include a handle assembly including a first actuator operatively coupled to the sheath to provide relative movement between the plurality of movable members and distal ends of the plurality of support arms. The handle assembly may also include a second actuator operatively coupled to the sheath to provide relative movement between the plurality of movable members and distal ends of the plurality of support arms. The device may also include a biasing member operatively coupled between the first actuator and the second actuator. The biasing member may be configured to deform to facilitate movement of the end effector from at least one of the extended state to a further extended state, and the retracted state to a further retracted state.

In addition or alternatively, the device may include one or more of the features below. The biasing member may provide a lost motion connection between the first actuator and the second actuator. The first actuator may be configured to move in a distal direction relative to a handle body to move the sheath and transition the end effector to the retracted state. The first actuator may be configured to transfer a force to the biasing member when the first actuator moves in the distal direction. The biasing member may be configured to deform due to the force when the force on the first actuator exceeds a predetermined value. The first actuator may be configured to move in a proximal direction relative to the handle body to move the sheath and transition the end effector to the extended state. The second actuator may be configured to transfer a force to deform the biasing member when the second actuator moves in the proximal direction.

It may be understood that both the foregoing general description and the following detailed description are exemplary and explanatory only and are not restrictive of the claimed features.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 1A is a cross-sectional side view of a portion of a retrieval device, in accordance with aspects of the present disclosure.

FIG. 1B is a perspective view of a portion of a retrieval device, in accordance with aspects of the present disclosure.

FIG. 1C is another cross-sectional side view of the portion of the retrieval device of FIG. 1A, in accordance with aspects of the present disclosure.

FIG. 1D is another perspective view of the portion of the retrieval device of FIG. 1B, in accordance with aspects of the present disclosure.

FIG. 2A is a perspective view of a portion of another retrieval device, in accordance with aspects of the present disclosure.

FIG. 2B is another perspective view of the portion of the retrieval device of FIG. 2A, in accordance with aspects of the present disclosure.

FIG. 4B is another perspective view of the portion of the retrieval device of FIG. 4A, in accordance with aspects of the present disclosure.

FIG. 5A is a side view of a portion of a retrieval device, in accordance with aspects of the present disclosure.

FIG. 5B is a perspective view of a component of the portion of the retrieval device of FIG. 5A, in accordance with aspects of the present disclosure.

FIG. 6A is a perspective view of a portion of a retrieval device, in accordance with aspects of the present disclosure.

FIG. 6B is a perspective view of a component of the portion of the retrieval device of FIG. 6A, in accordance with aspects of the present disclosure.

FIG. 13 is a partial cross-sectional side view of portions of the retrieval device of FIG. 9 in an extended state, in accordance with aspects of the present disclosure.

FIG. 14 is a partial cross-sectional side view of portions of the retrieval device of FIG. 9 in a further extended state, in accordance with aspects of the present disclosure.

FIG. 15 is a partial cross-sectional side view of portions of the retrieval device of FIG. 9, in a retracted state, in accordance with aspects of the present disclosure.

FIG. 16 is a partial cross-sectional side view of a portion of a retrieval device of FIG. 9 in a further retracted state, in accordance with aspects of the present disclosure.

FIG. 19 is a partial cross-sectional side view of a portion of the retrieval device of FIG. 18 in in a further extended state, in accordance with aspects of the present disclosure.

DETAILED DESCRIPTION

Figure 3A:
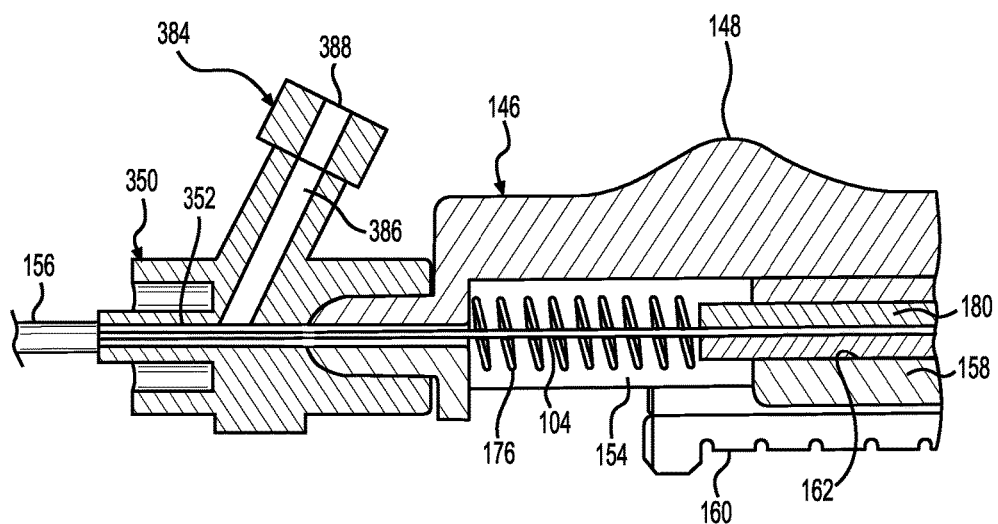
FIG. 3A is a cross-sectional side view of a portion of a retrieval device, in accordance with aspects of the present disclosure.

Reference will now be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a patient. By contrast, the term "proximal" refers to a portion closest to the user when placing the device into the patient.

FIGS. 1A-1D show portions of a retrieval device 100. Retrieval device 100 may include a sheath 102 including a distal end and a proximal end. Retrieval device 100 may also include an end effector 142 at the distal end of sheath 102. At least a portion of end effector 142 may be movable relative to sheath 102 between an extended state and a retracted state. End effector 142 may include a support member 130 coupled to the distal end of sheath 102 and a movable member 106 extending from support member 130. Retrieval device 100 may also include a handle assembly 144 at the proximal end of sheath 102. Handle assembly 144 may include an actuation member 146 for moving end effector 142 between the extended state and the retracted state. Retrieval device 100 may also include a biasing member 176 coupled to at least one of actuation member 146 and sheath 102. Biasing member 176 may control a force exerted by one of movable member 106 and support member 130 on the other of movable member 106 and support member 130, due to relative movement between movable member 106 and support member 130.

Sheath 102 may be an outer sheath. Outer sheath 102 may include a longitudinally-extending lumen 136. Outer sheath 102 may be, for example, a hollow tube. Outer sheath 102 may be made of a polymer material, metal, or a combination of materials.

Retrieval device 100 may also include a shaft or drive member 104. Drive member 104 may extend through lumen 136 of outer sheath 102. Drive member 104 may be elongated, and may include, for example, a wire, braid, shaft, and or any other suitable drive member configured to transfer translational and/or rotational forces from its proximal end to its distal end.

Retrieval device 100 may also include first, second, and third movable members 106, 108, and 110. Each of first, second, and third movable members 106, 108, and 110 may include a first proximal portion 112, 114, and 116, an intermediate portion including a reverse, U-shaped, or 180 degree bend 118, 120, and 122, and a second proximal portion 124, 126, and 128. While three movable members are shown, one or more additional movable members may also be included. It is also contemplated that fewer than three movable members may be included.

Each of movable members 106, 108, and 110 may be formed of any suitable material including, but not limited to, metals, polymers, or a combination of materials. For example, one or more of movable members 106, 108, and 110 may be formed with a shape memory material, such as Nitinol, and may be treated to possess an internal bias causing one or more of movable members 106, 108, and 110 to move radially outwardly away from the longitudinal axis of outer sheath 102 in the absence of a constraining force.

Each of movable members 106, 108, and 110 may have any suitable cross-sectional shape, including cylindrical, elliptical, polygonal, and/or irregular. One or more of movable members 106, 108, and 110 may include a portion flattened, machined, extruded, drawn, and/or etched into a different profile than a remaining portion. One or more of movable members 106, 108, and 110 may be slotted to allow deflection or directional bending. Exterior surfaces of one or more of movable members 106, 108, and 110 may be roughened, notched, slotted, etched, sand-blasted, or otherwise modified to provide a better gripping surface.

Movable members 106, 108, and 110 may be attached to drive member 104. For example, proximal ends of movable members 106, 108, and 110 may be attached to the distal end of drive member 104. The attachment may be provided by one or more of a splice joint, adhesives, melting, welding, crimping, joining using a heat shrinkable sleeve, and/or any other suitable attachment mechanism.

Retrieval device 100 may also include first, second, and third support members 130, 132, and 134. Each of support members 130, 132, and 134 may include a lumen (not shown) extending longitudinally therethrough. For example, one or more of support members 130, 132, and 134 may be a hollow tube. Support members 130, 132, and 134 may be disposed circumferentially about the longitudinal axis of outer sheath 102. Longitudinal axes of support members 130, 132, and 134 may be disposed at equal intervals circumferentially about the longitudinal axis of outer sheath 102. It should, however, be noted that any other suitable number of support members and spacing configurations may alternatively be utilized.

Each of support members 130, 132, and 134 may have any suitable cross-sectional shape, including cylindrical elliptical, polygonal, and/or irregular. One or more of support members 130, 132, and 134 may include a portion flattened, machined, extruded, drawn, and/or etched into a different profile than a remaining portion. Support members 130, 132, and 134 may be made of a flexible material, so that they can bend when being inserted into and through tortuous passages in a subject's anatomy. One or more of support members 130, 132, and 134 may be slotted to allow deflection or directional bending. Exterior surfaces of one or more of support members 130, 132, and 134 may be roughened, notched, slotted, etched, sand-blasted, or otherwise modified to provide a better gripping surface. Support members 130, 132, and 134 may be made of any suitable material, including a polymer such as polyimide, or polyethylene terephthalate.

Proximal portions of support members 130, 132, and 134 may be received in lumen 136 of outer sheath 102. For example, proximal portions of one or more of support members 130, 132, and 134 may be covered by a distal portion of outer sheath 102, leaving a distal length exposed from the distal end of outer sheath 102. Proximal portions of support members 130, 132, and 134 may be fixed relative to outer sheath 102. For example, the distal end of outer sheath 102 may include a coupler 138 for holding support members 130, 132, and 134. Coupler 138 may include a heat-shrinkable sleeve and/or adhesive, such as an ultraviolet light curable adhesive or cyanoacrylate. Coupler 138 may keep the proximal ends of support members 130, 132, and 134 stationary relative to the distal end of outer sheath 102, while allowing distal portions of the support members 130, 132, and 134 to move relative to the distal end of outer sheath 102 and relative to one another.

Each of support members 130, 132, and 134 may contact the other two support members. For example, each of the proximal portions of the support members 130, 132, and 134 may contact the proximal portions of the other two support members, such that support members 130, 132, and 134 may have a triangular arrangement around the longitudinal axis of outer sheath 102. Longitudinal axes of support members 130, 132, and 134 may form vertices of a triangle, and portions of the longitudinal axes may be parallel. Distal portions of support members 130, 132, and 134 may be movable towards and away from the longitudinal axis of outer sheath 102. The number of support members 130, 132, and 134 may be equal to the number of movable members 106, 108, and 110. It is contemplated that the number of support members and movable members may vary based on the type of procedure being performed.

Each of movable members 106, 108, and 110 may extend distally from drive member 104, and may enter a lumen of one of support members 130, 132, and 134 at its proximal end. Each of movable members 106, 108, and 110 may extend distally through the lumen, and may exit the lumen at the distal end of one of support members 130, 132, and 134. There each of movable members 106, 108, and 110 may transition into bend 118, 120, and 122, respectively. Each of movable members 106, 108, and 110 may then enter the lumen through the distal end of another one of support members 130, 132, and 134. Each of movable members 106, 108, and 110 may extend proximally through the lumen, and may exit the lumen at the proximal end of one of support members 130, 132, and 134. After exiting, each of movable members 106, 108, and 110 may be received by a coupler 140. For example, coupler 140 may be positioned distally of the distal end of drive member 104. Coupler 140 may be a tube, and may include a lumen (not shown) configured to receive movable members 106, 108, and 110. Movable members 106, 108, and 110 may be attached to coupler 140 by adhesive, melting, welding, friction fit, heat-shrinking coupler 140, and/or any other suitable form of attachment. Coupler 140 may be fixed in place relative to the distal end of drive member 104 or may be configured to translate such that the position of coupler 140 changes relative to the distal ends of support members 130, 132, and 134.

Portions of movable members 106, 108, and 110 extending distally from drive member 104 may extend alongside surfaces of coupler 140, and may contact the side surfaces of coupler 140. Coupler 140 may space those portions of movable members 106, 108, and 110 apart from the longitudinal axis of outer sheath 102, to help guide movable members 106, 108, and 110 into the lumens of support members 130, 132, and 134. Coupler 140 may contain grooves, slots, or other recessed features to accommodate portions of movable members 106, 108, and 110. Movable members 106, 108, and 110 may extend alongside and/or contacts surfaces of coupler 140 in a longitudinal, helical, wound, twisted, or other suitable orientation.

Movable members 106, 108, and 110, and support members 130, 132, and 134, may form capture members of end effector 142. End effector 142 may form a basket. In FIG. 1B, end effector 142 is shown in a retracted and contracted state. End effector 142 may be moved into its retracted and contracted state by moving drive member 104 proximally relative to outer sheath 102. In the retracted and contracted state, bends 118, 120, and 122 may be at or adjacent to distal ends of support members 130, 132, and 134. Longitudinal axes of support members 130, 132, and 134 may be substantially parallel, and both proximal and distal portions of each of support members 130, 132, and 134 may be in contact with the other support members. Portions of movable members 106, 108, and 110 in the lumens of support members 130, 132, and 134 may be substantially parallel. Support members 130, 132, and 134, and/or outer sheath 102 may counteract the inherent bias in movable members 106, 108, and 110, keeping portions of movable members 106, 108, and 110 from bending radially outwardly from the longitudinal axis of outer sheath 102.

In the retracted and contracted state, the distal end of coupler 140 may be spaced from proximal ends of support members 130, 132, and 134 by a distance. That distance may be about 12 millimeters, although other distances may also be used. The proximal end of coupler 140 may be spaced from the distal end of drive member 104 by a distance. That distance may be about 16 millimeters, although other distances may also be used. The two distances may vary based on the procedure being performed with retrieval device 100.

In FIG. 1D, end effector 142 is shown in an extended and expanded state. In the extended and expanded state, portions of movable members 106, 108, and 110 may be exposed from the distal ends of the support members 130, 132, and 134. Once exposed, movable members 106, 108, and 110 may move radially outwardly from the longitudinal axis of outer sheath 102 due to inherent radially outward biasing in movable members 106, 108, and 110. Radially outward movement of movable members 106, 108, and 110 may cause a radially outward movement of support members 130, 132, and 134. Alternatively, support members 130, 132, and 134 may be biased radially outwardly, and movable members 106, 108, and 110 may urge support members 130, 132, and 134 into the retracted and contracted state.

In the extended and expanded state of end effector 142, exposed portions of movable members 106, 108, and 110 may form bridges between the distal ends of support members 130, 132, and 134. Each bridge may extend distally from the distal end of a given support member, and may be received in the distal end of an adjacent support member. Each bridge and its corresponding pair of support members may form a side loop of end effector 142. Three side loops are shown in FIG. 1D. The bridges may form a front loop of end effector 142. Materials may enter end effector 142 through one or more of the front loop and the side loops. By adding additional movable members and support members, additional side loops can be created. It is also contemplated that end effector 142 may include fewer movable members and support members. For example, end effector 142 may include two movable members and two support members. The bridges defined by the two movable members may form a front loop.

Outer sheath 102 and support members 130, 132, and 134 may be moved proximally relative to movable members 106, 108, and 110 to extend end effector 142, allowing end effector 142 to move to its extended and expanded state. Drive member 104 may be moved distally relative to outer sheath 102 to extend end effector 142, allowing end effector 142 to move to its extended and expanded state. The expansion may be due to inherent radially outward biasing in one or more of movable members 106, 108, and 110.

Extension and expansion of end effector 142 may occur in phases. Starting from the retracted and contracted state shown in FIG. 1B, a first phase of the extension and expansion of end effector 142 may begin with movement of drive member 104 distally relative to outer sheath 102 and support members 130, 132, and 134. The relative movement of drive member 104 may cause movable members 106, 108, and 110 and coupler 140 to move distally relative to outer sheath 102. The movement of drive member 104, movable members 106, 108, and 100, and coupler 140 may be translational. First proximal portions 112, 114, and 116, and second proximal portions 124, 126, and 128 may enter the lumens of support members 130, 132, and 134 through proximal openings (not shown) in support members 130, 132, and 134. Bends 118, 120, and 122 may emerge from, or extend further out from, distal ends of support members 130, 132, and 134.

Coupler 140 may move with movable members 106, 108, and 110 relative to outer sheath 102 and support members 130, 132, and 134. When coupler 140 has traveled a distance toward proximal ends of support members 130, 132, and 134, the distance being substantially equal to the distance between the distal end of coupler 140 and the proximal ends of support members 130, 132, and 134 in FIG. 1B, further proximal movement of coupler 140 may be halted as coupler 140 reaches a point where it prevents further spreading of second proximal portions 124, 126, and 128, thus preventing second proximal portions 124, 126, and 128 from entering the lumens of support members 130, 132, and 134. At the end of the first phase of extension and expansion, bends 118, 120, and 122 may be spaced from distal ends of support members 130, 132, and 134 by a distance substantially equal to the distance between proximal ends of support members 130, 132, and 134 and the distal end of coupler 140 in FIG. 1B.

A second phase of extension and expansion of end effector 142 may begin after distal movement of coupler 140 has been halted. During the second phase, further distal movement of drive member 104 relative to outer sheath 102 and support members 130, 132, and 134 may drive distal movement of first proximal portions 112, 114, and 116 relative to outer sheath 102 and support members 130, 132, and 134. During the second phase, second proximal portions 124, 126, and 128 may remain fixed relative to support members 130, 132, and 134. First proximal portions 112, 114, and 116 may enter lumens in support members 130, 132, and 134 via proximal openings (not shown) in support members 130, 132, and 134, and may exit the lumens via distal openings (not shown), thereby increasing the lengths of the bridges of end effector 142, and expanding the sizes of front and side loops of end effector 142. The second phase of extension and expansion may continue over a distance substantially equal to the distance between the proximal end of coupler 140, and an intermediate position between the proximal end of coupler 140 and the distal end of drive member 104 in FIG. 1B. Distal movement of drive member 104 may be halted where the distal end of drive member 104 prevents first proximal portions 112, 114, and 116 from spreading far enough apart to enter the proximal ends of support members 130, 132, and 134. Additionally or alternatively, distal movement may be halted due to coupler 140 obstructing further distal movement of first proximal portions 112, 114, and 116 and/or drive member 104. Additionally or alternatively, distal movement may halt due to operation of a handle assembly of retrieval device 100, such as handle assembly 144 described further below.

Moving end effector 142 back to the retracted and contracted state may be accomplished by moving outer sheath 102 and support members 130, 132, and 134 distally relative to movable members 106, 108, and 110. Movement from the extended and expanded state to the retracted and contracted state may also occur in phases. A first phase of the retraction and contraction of end effector 142 may begin with drive member 104 moving proximally relative to the outer sheath 102. This may cause first proximal portions 112, 114, and 116 to move proximally relative to outer sheath 102 and support members 130, 132, and 134. Distal portions of movable members 106, 108, and 110 may enter lumens at the distal ends of support members 130, 132, and 134. Second proximal portions 124, 126, and 128, and coupler 140 may remain stationary relative to support members 130, 132, and 134. The lengths of the bridges of end effector 142 may decrease. Movable members 106, 108, and 110, and support members 130, 132, and 134 may move radially inwardly. Thus, the front loop and the side loops of end effector 142 may decrease in size.

The first phase of the retraction and contraction of end effector 142 may take place over a distance substantially equal to the distance between a proximal end of coupler 140, and an intermediate position between the proximal end of coupler 140 and the distal end of drive member 104, in FIG. 1B. Once that distance has been covered, a second phase of the retraction and contraction may take place with continued movement of drive member 104 proximally relative to outer sheath 102 and support members 130, 132, and 134. The continued movement may cause movable members 106, 108, and 110 and coupler 140 to move distally relative to outer sheath 102 and support members 130, 132, and 134. The movement of drive member 104, movable members 106, 108, and 110, and coupler 140 may be translational. For example, drive member 104, first proximal portions 112, 114, and 116, second proximal portions 124, 126, and 128, and coupler 140, may move proximally relative to outer sheath 102 and support members 130, 132, and 134 during the second phase. Proximal parts of first proximal portions 112, 114, and 116, and second proximal portions 124, 126, and 128, may exit the lumens of support members 130, 132, and 134 at proximal ends of support members 130, 132, and 134. Distal portions of movable members 106, 108, and 110, including parts at or near both sides of bends 118, 120, and 122, may enter into, or move further past, the distal ends of support members 130, 132, and 134. The lengths of the bridges may decrease as the exposed lengths of movable members 106, 108, and 110 decrease. As the bridges of end effector 142 shrink, movable members 106, 108, and 110 and support members 130, 132, and 134, may contract radially inwardly toward the longitudinal axis of outer sheath 102. The front loop and side loops of end effector 142 may also shrink in size.

Coupler 140 may move with movable members 106, 108, and 110 relative to outer sheath 102 and support members 130, 132, and 134. When coupler 140 has traveled a distance relative to outer sheath 102 and support members 130, 132, and 134, the distance being substantially equal to the distance between proximal ends of support members 130, 132, and 134 and the distal end of coupler 140 in FIG. 1B, further proximal movement of coupler 140 may be halted as bends 118, 120, and 122 reach a point where they prevent further proximal movement of movable members 106, 108, and 110 as they engage distal ends of support members 130, 132, and 134. Additionally or alternatively, further movement may be halted by operation of handle assembly 144. At the end of the second phase of retraction and contraction, the state shown in FIG. 1B is attained.

FIGS. 1A and 1C show handle assembly 144. Handle assembly 144 may include actuation member 146. Actuation member 146 may have a protrusion 148 on its upper surface, on which the user may exert forces on actuation member 146 using his or her thumb. Actuation member 146 may be coupled to a proximal portion of outer sheath 102 by a connector 150, which may include a male luer fitting. Drive member 104 may extend proximally through a lumen 152 in connector 150, and a passage 154 in actuation member 146. A strain relief member 156 may be coupled to connector 150, and may extend at least partially over the proximal portion of outer sheath 102. Outer sheath 102 may be moved distally relative to drive member 104 by moving actuation member 146 distally, and proximally by moving actuation member 146 proximally.

Actuation member 146 may slidably engage a handle body 158. For example, actuation member 146 may rest on handle body 158, and may slide distally and proximally relative to handle body 158. Handle body 158 may be fixedly coupled to a handle cover 160. Thus, actuation member 146 may also slide distally and proximally relative to handle cover 160. A proximal portion of drive member 104 may extend through a longitudinally-extending passage 162 in handle body 158. At its proximal end, handle body 158 may form a vise 164, or any other suitable holding mechanism. When vise 164 closes, handle body 158 and drive member 104 may be fixedly coupled. An end cap 166 may be placed onto proximal ends of handle body 158 and handle cover 160, to help close the vise around drive member 104. Handle cover 160 may include an externally threaded portion (not shown), and end cap 166 may include complementary internal threading (not shown), so end cap 166 may be screwed onto handle cover 160.

When actuation member 146 is moved distally relative to handle body 158 and handle cover 160, outer sheath 102 and support members 130, 132, and 134 may move distally relative to drive member 104 and movable members 106, 108, and 110. The distally moving support members 130, 132, and 134 may slide over portions of movable members 106, 108, and 110, putting end effector 142 in its retracted and contracted state.

A stroke limiter 168 may be coupled to a stop or abutment 172 on actuation member 146, such that stroke limiter 168 may move with actuation member 146. Alternatively, stroke limiter 168 may be coupled to a distal stop or abutment 170 on handle body 158, such that actuation member 146 may move relative to stroke limiter 168. Stroke limiter 168 may, for example, be coupled by snap-fit engagement to a recess in handle body 158 or actuation member 146. As actuation member 146 moves distally relative to handle body 158 and handle cover 160, the distance between stops 170 and 172 may decrease, as well as the distance between distal ends of support members 130, 132, and 134, and bends 118, 120, and 122 of movable members 106, 108, and 110. Once the distal ends of support members 130, 132, and 134 move far enough distally to reach bends 118, 120, and 122, further distal movement may force support members 130, 132, and 134 against bends 118, 120, and 122. If that force is strong enough, bends 118, 120, and 122 may damage support members 130, 132, and 134 by, for example, tearing into the distal ends of support members 130, 132, and 134. Stroke limiter 168 may prevent such damage by engaging stops 170 and 172, thus limiting distal movement of actuation member 146 relative to handle body 158 and handle cover 160, and thereby limiting distal movement of support members 130, 132, and 134 relative to bends 118, 120, and 122 of movable members 106, 108, and 110.

Handle body 158 may also include a stop or abutment 174, for engaging stop 172 of actuation member 146 to limit proximal travel of actuation member 146 relative to handle body 158, thereby limiting proximal movement of support members 130, 132, and 134 relative to movable members 106, 108, and 110. As actuation member 146 moves proximally relative to handle body 158 and handle cover 160, the distance between stops 172 and 174 may decrease, as well as the distance between proximal ends of support members 130, 132, and 134 and coupler 140, and/or between proximal ends of support members 130, 132, and 134 and portions of movable members 106, 108, and 110 leading to coupler 140.

Once the proximal ends of support members 130, 132, and 134 move far enough proximally to reach full extension and expansion of end effector 142, further proximal movement may be unnecessary and/or may force support members 130, 132, and 134 against coupler 140 and/or portions of movable members 106, 108, and 110 leading to coupler 140. If that force is strong enough, coupler 140 and/or portions of movable member 106, 108, and 110 may damage support members 130, 132, and 134 by, for example, tearing into the proximal ends of support members 130, 132, and 134. Stops 172 and 174 may prevent such damage by engaging one another to limit excess proximal movement of actuation member 146 relative to handle body 158 and handle cover 160, thereby limiting proximal movement of support members 130, 132, and 134 relative to coupler 140 and/or portions of movable members 106, 108, and 110.

A biasing member 176 may be operatively coupled to actuation member 146 and handle body 158. For example, biasing member 176 may surround at least a portion of drive member 104. A distal end of biasing member 176 may engage actuation member 146. In one arrangement, the distal end of biasing member 176 may engage a wall 178 of actuation member 146. A proximal end of biasing member 176 may engage handle body 158. The proximal end of biasing member 176 may engage a distal end of handle body 158, a distal end of a sleeve 180 around drive member 104 that is received in passage 162 of handle body 158, and/or a portion of handle cover 160.

Biasing member 176 may exert a force biasing actuation member 146 distally relative to handle body 158 and handle cover 160. Biasing member 176 may tend to force actuation member 146 distally relative to handle body 158 and handle cover 160 until stops 170 and 172 are forced against ends of stroke limiter 168. As such, biasing member 176 may tend to force end effector 142 into its retracted and contracted state, preventing inadvertent extension and expansion of end effector 142.

It is contemplated that biasing member 176 may be supported around drive member 104 by a flared tube or other suitable sleeve (not shown) between the outer surface of drive member 104 and the internal diameter of biasing member 176. Alternatively, biasing member 176 may include a coil tension spring (not shown) whose ends may be coupled to stops 170 and 172. Wire forming the tension spring may have a flat, round, or any other suitable cross-sectional shape. Biasing member 176 may be made of stainless steel, spring steel, or any other suitable material. Alternatively, biasing member 176 may include an elastic tube made of silicone or rubber.

Biasing member 176 is shown in a rest state in FIG. 1A, and in a biasing state in FIG. 1C. In use, a user may overcome the biasing force of biasing member 176 by forcing actuation member 146 proximally relative to handle body 158 and handle cover 160 (FIG. 1C). The user may do so when seeking to extend and expand end effector 142 to capture an object 182 (FIG. 1D), such as a stone. If the user then attempts to close end effector 142 around object 182 by forcing actuation member 146 distally relative to handle body 158 and handle cover 160, support members 130, 132, and 134 may be forced distally relative to movable members 106, 108, and 110, bringing movable members 106, 108, and 110 radially inward. Movable members 106, 108, and 110 may at some point engage the outer surface of object 182. If the user continues to force actuation member 146 distally, support members 130, 132, and 134 may continue to move distally. If object 182 prevents movable members 106, 108, and 110 from moving radially inward as support members 130, 132, and 134 move distally, the distal movement of support members 130, 132, and 134 may bring one or more of movable members 106, 108, and 110 against one or more of support members 130, 132, and 134 with a greater amount of force than support members 130, 132, and 134 can withstand. If this happens, the distal ends of one or more of support members 130, 132, and 134 may tear, break, flare or suffer other damage.

Biasing member 176 may reduce the likelihood of damaging one or more of support members 130, 132, and 134 through excessive forceful engagement with one or more of movable members 106, 108, and 110. Biasing member 176 may also reduce the likelihood of object 182 escaping from end effector 142 due to insufficient closing force being applied to end effector 142.

For example, once the user has extended and expanded end effector 142 to capture object 182, the user may let go of actuation member 146 instead of actively pushing actuation member 146 distally. Biasing member 176 may move actuation member 146 distally with a predetermined force, thus closing end effector 142 around object 182 with a predetermined closing force. When object 182 prevents movable members 106, 108, and 110 from moving radially inwardly any further, distal movement of actuation member 146, and of support members 130, 132, and 134, may cease.

The predetermined closing force exerted by biasing member 176 may limit the amount of force applied to end effector 142, and in particular, to support members 130, 132, and 134 by movable members 106, 108, and 110. The predetermined closing force may be selected to ensure that the forces between movable members 106, 108, and 110 and support members 130, 132, and 134 are limited such that movable members 106, 108, and 110 will not damage support members 130, 132, and 134. If an additional amount of closing force is required, the user may remove end cap 166, grasp the proximal end of drive member 104, and pull drive member 104 distally relative to actuation member 146. Additionally or alternatively, the user may exert more closing force by pushing actuation member 146 distally to supplement the biasing force exerted by biasing member 176. Stroke limiter 168 will eventually prohibit further movement of actuation member 146 distally when end effector 142 reaches the fully retracted and contracted state.

FIGS. 2A and 2B show movable or capture members 208 and 210 that are alternatives of movable members 108 and 110 (FIGS. 1A-1D). Movable members 208 and 210 may not be coupled to drive member 104. Rather, movable members 208 and 210 may include proximal portions 226 and 228, respectively, coupled on their proximal ends to coupler 140. Movable members 208 and 210 may also include opposite ends fixed within support member 134. Those ends may be fixed within support member 134 by any suitable attachment mechanism. For example, the ends may be fixed within support member 134 by an adhesive, support member 134 may be crimped around the ends, and/or support member 134 may be heat shrunk onto the ends.

Between their ends, movable members 208 and 210 may include reverse, U-shaped, or 180 degree bends 220 and 222, respectively. Proximal portion 226 of movable member 208 may be slidable into and out of support member 132, and proximal portion 228 of movable member 210 may be slidable into and out of support member 130. The portions of movable members 208 and 210 on the other sides of their respective bends 220 and 222, extending through and fixedly coupled to support member 134, may remain fixed relative to support member 134.

FIG. 2A shows movable members 118, 208, and 210, and support members 130, 132, and 134 in a retracted and contracted state. From that state, moving outer sheath 102 and support members 130, 132, and 134 proximally relative to drive member 104 and movable member 106, may expose portions of movable member 106 from distal ends of support members 130 and 132. The inherent bias in movable member 106 may cause support members 130 and 132 to expand radially outwardly from the longitudinal axis of outer sheath 102. Portions of movable members 208 and 210 in support members 130 and 132 may be exposed during the radially outward movement of support members 130 and 132.

Support member 134, however, may remain substantially stationary. The inherent bias in movable member 106, while being capable of deflecting support members 130 and 132, may be insufficient for deflecting support member 134. Support member 134 may act as a stationary point and/or guide for positioning against object 182. Support member 134 may help keep object 182 substantially stationary during closing of movable members 208 and 210 and support members 130 and 132 around object 182. If support member 134 does not remain substantially stationary during closing, one or more of movable members 106, 208, and 210 and/or support members 130, 132, and 134 may potentially engage object 182 before another of movable members 106, 208, and 210 and/or support members 130, 132, and 134, causing object 182 to move. If object 182 is small enough relative to the openings defined by movable members 106, 208, and 210 and/or support members 130, 132, and 134, object 182 may escape through one of those openings. By keeping support member 134 substantially stationary, the likelihood of losing object 182 may be reduced, since support member 134 may help keep object 182 relatively still during closing. Further the lack of movement of support member 134 may help limit the size of front and side openings defined by movable members 106, 208, and 210 and/or support members 130, 132, and 134, providing additional assistance with respect to retrieving small objects.

It is contemplated that support member 134 may have a visual feature that distinguishes it from support members 130 and 132, to help the user identify the support member that will remain substantially stationary during opening and closing. For example, support member 134 may have a different color than support members 130 and 132. It should be understood that while support member 134 may remain substantially stationary during opening and closing, support member 134 may be as flexible as support members 130 and 132. For example, all three support members 130, 132, and 134 may be made of the same or similar materials.

FIG. 3A shows a connector 350 that is an alternative of connector 150 (FIGS. 1A and 1C). Connector 350 may be a male luer fitting. Connector 350 may be fixedly coupled to a distal portion of actuation member 146. Connector 350 may include a lumen 352 in which a portion of drive member 104 may be received. Lumen 352 may be in fluid communication with lumen 136 of outer sheath 102. Connector 350 may include a port 384 with a lumen 386 having an inlet 388. Lumen 386 may be in fluid communication with lumen 352 of connector 350. A fluid (not shown) may be introduced into lumen 386 via inlet 388. It is contemplated that inlet 388 may include a valve or seal (not shown) for limiting or preventing leakage of the fluid from inlet 388. The fluid may travel through lumen 386 into lumen 352. It is contemplated that a valve or seal (not shown) may be provided around drive member 104 at a position proximal to lumen 386 to limit or prevent fluid flow proximally out of the proximal end of lumen 352.

The fluid may flow distally through lumen 352 into lumen 136 of outer sheath 102. The fluid may be introduced with sufficient pressure to force the fluid to the distal end of outer sheath 102. For example, the fluid may flow through one or more gaps between support members 130, 132, and 134, and out of the distal end of outer sheath 102. Additionally or alternatively, the fluid may flow through one or more of support members 130, 132, and 134, and out of the distal end of one or more of support members 130, 132, and 134. The fluid may be emitted while the support members 130, 132, and 134 are retracted or collapsed, or extended and expanded. It is contemplated that one or more of support members 130, 132, and 134 may include one or more openings (not shown) between their proximal and distal ends through which the fluid may be secreted.

Figure 3B:
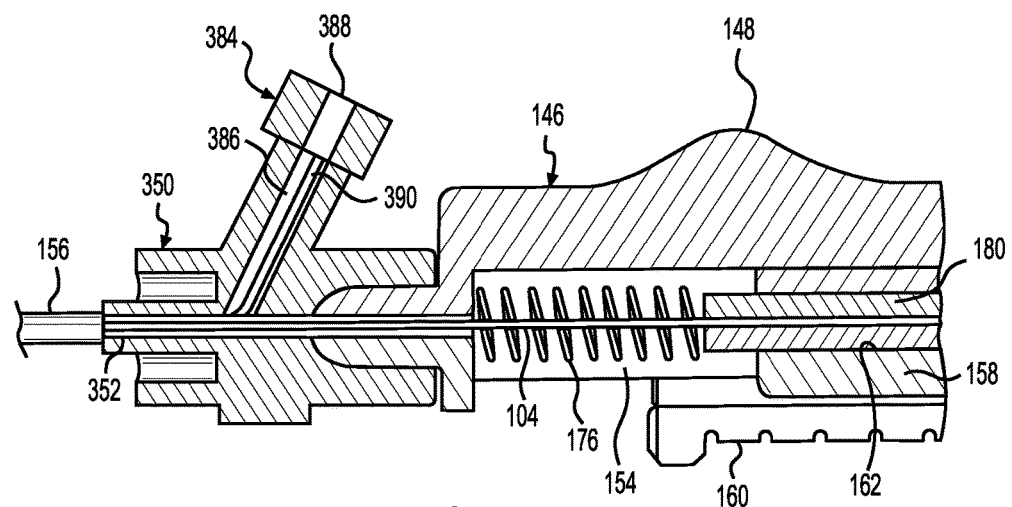
FIG. 3B is another cross-sectional side view of the portion of the retrieval device of FIG. 3A, in accordance with aspects of the present disclosure.

FIG. 3B shows connector 350 with an inner tube or lumen 390 extending through lumen 386. A fluid may be introduced into inner lumen 390 via inlet 388. The fluid may travel through inner lumen 390. Inner lumen 390 may extend distally through lumen 352 of connector 350 and lumen 136 of outer sheath 102. It is contemplated that inner lumen 390 may terminate in outer sheath 102 proximal of support members 130, 132, and 134. Fluid injected into inner lumen 390 may flow into outer sheath 102 through one or more gaps between support members 130, 132, and 134, and out of the distal end of outer sheath 102. Additionally or alternatively, the fluid may flow through one or more of support members 130, 132, and 134 and out of the distal end of one or more of support members 130, 132, and 134.

Alternatively, inner lumen 390 may extend through a gap between support members 130, 132, and 134, terminating within the gap or at the distal end of outer sheath 102. The fluid may flow through the gap and out of outer sheath 102. It is also contemplated that inner lumen 390 may extend distally beyond the distal end of outer sheath 102.

Alternatively, inner lumen 390 may terminate at one of support members 130, 132, and 134. For example, inner lumen 390 may terminate at a proximal end, distal end, or intermediate portion of one of support members 130, 132, and 134. The injected fluid may flow through inner lumen 390 into the support member, and out the distal end of the support member. It is also contemplated that inner lumen 390 may extend distally beyond the distal end of the support member.

Additionally or alternatively, there may be a plurality of inner lumens (not shown), or inner lumen 390 may branch off into a plurality of inner lumens. It is contemplated that one or more of the inner lumens may terminate in outer sheath 102 proximal of support members 130, 132, and 134. Additionally or alternatively, one or more of the inner lumens may extend through a gap between support members 130, 132, and 134. Additionally or alternatively, one or more of the inner lumens may terminate at one or more of support members 130, 132, and 134.

The fluid may include, for example, a gel. The gel may include a water-soluble polymer that may form a plug in a subject's body. One example of such a gel is BACKSTOP™ from Boston Scientific. The fluid may be reverse thermosensitive. Thus, the fluid may be soft and easy to inject at room temperature, and more viscous at body temperature. When introduced into the subject's body, the fluid may help trap small objects or fragments of objects. This may assist with keeping such objects in contact with movable members 106, 108, and 110, support members 130, 132, and 134, and/or outer sheath 102. Additionally or alternatively, the fluid may trap multiple fragments and form them into a larger mass for easier capture and handling.

In use, after a user has captured object 182 in end effector 142, the user may perform lithotripsy on object 182 to break it apart into smaller pieces. Prior to, during, or after performing lithotripsy, the fluid may be directed toward the area around object 182. As the fluid becomes more viscous due to the subject's body heat, the pieces of object 182 may be caught and held by the fluid. Thus, end effector 142 may exert more of a holding force on the pieces. When the procedure is completed, the fluid may be removed from device surfaces using a saline wash. The saline may, for example, be introduced through port 384 to flush the fluid out.

Figure 4A:
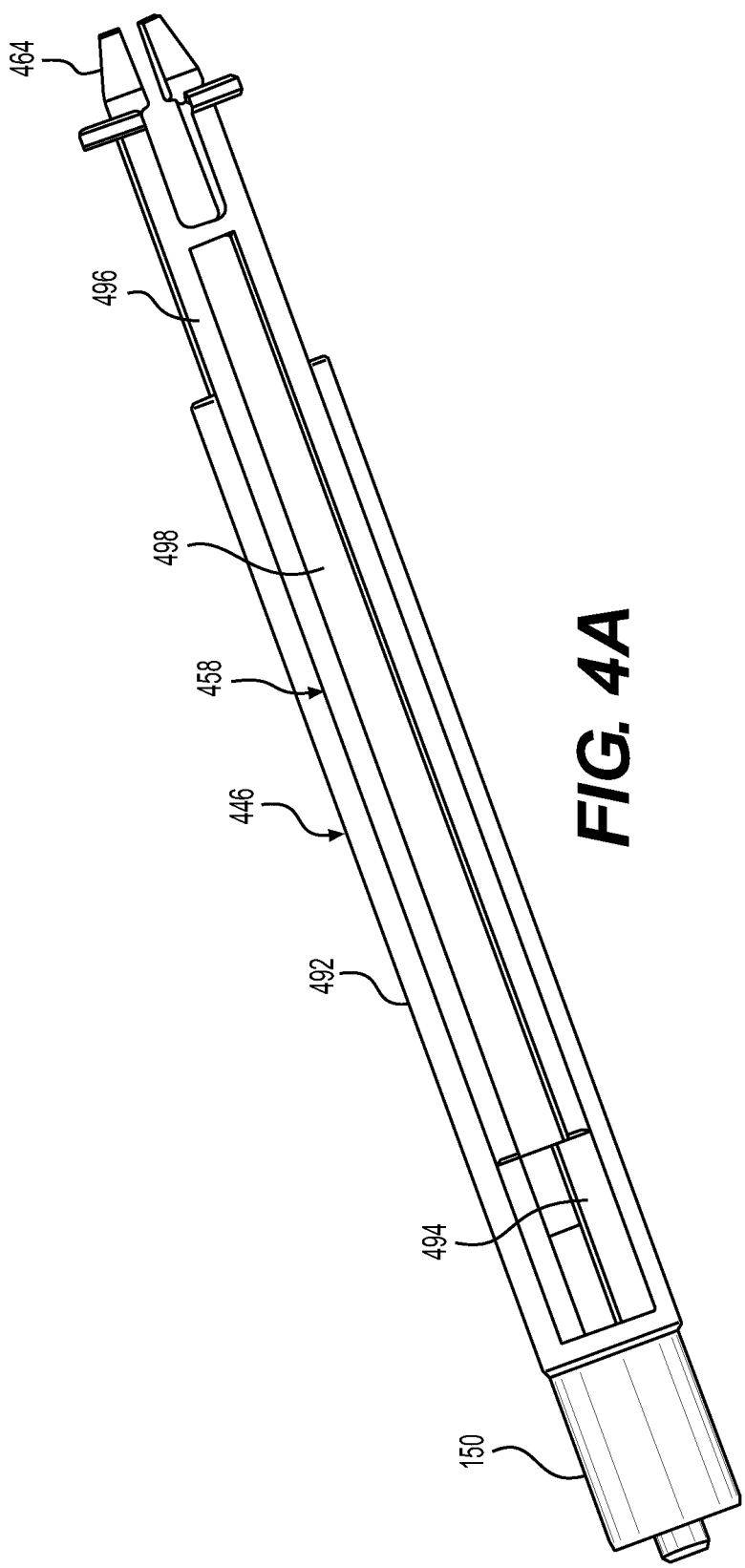
FIG. 4A is a perspective view of a portion of a retrieval device, in accordance with aspects of the present disclosure.

FIGS. 4A and 4B show an actuation member 446 and a handle body 458, that are alternatives of actuation member 146 and handle body 158 (FIGS. 1A and 1C), respectively. Connector 150 may be coupled to a distal end of actuation member 446. Actuation member 446 may include sidewalls 492 defining a slot 494. Handle body 458 may be slidably received in slot 494 for sliding between a first position (FIG. 4A), corresponding to an end effector retracted and contracted state, and a second position (FIG. 4B) corresponding to an end effector extended and expanded state. Handle body 458 may include sidewalls 496 defining a slot 498. It is contemplated that drive member 104 may extend proximally through connector 150, slot 494 of actuation member 446, and slot 498 of handle body 458. Handle body 458 may include a proximal vise 464 for gripping drive member 104.

FIGS. 5A and 5B show an outer sheath 502 that is an alternative of outer sheath 102. A portion of outer sheath 502 may be surrounded by a biasing member 503. Biasing member 503 may be a coil spring, such as a tension spring. A connector 505, which may be a female luer fitting, may be fixedly coupled to the portion of biasing member 503 extending through it using, for example, gluing, insert molding, heat-shrinking, crimping, and/or any other suitable form of attachment. Biasing member 503 may be made stainless steel, spring steel, or any other suitable material. Biasing member 503 may be made of wire having a flat, round, or any other suitable cross-sectional shape. Alternatively, biasing member 503 may include an elastic tube made of silicone or rubber.

A proximal end of connector 505 may be received by a distal end of connector 150. The portion of biasing member 503 distal to connector 505 may help relieve strain in the portion of outer sheath 502 extending distally from connector 505. By relieving strain, the distal portion of biasing member 503 may help prevent outer sheath 502 from kinking at or near connector 505. The portion of biasing member 503 proximal to connector 505, along with outer sheath 502, may extend into actuation members 146 or 446 and handle bodies 158 or 458 (FIGS. 4A and 4B), respectively.

The proximal end of biasing member 503 may be fixedly attached to outer sheath 502 using, for example, gluing, heat-shrinking, insert molding, crimping, and/or any other suitable form of attachment. Portions of biasing member 503 distal to the proximal end of biasing member 503 may be movable relative to the exterior surface of outer sheath 502. For example, while the proximal end of biasing member 503 may be fixedly attached to outer sheath 502, the distal end of biasing member 503 may move distally relative to outer sheath 502 during elongation and compression of biasing member 503. Biasing member 503 may be configured without gaps between adjacent turns of biasing member 503 when in its rest state. Once it has been elongated, biasing member 503 may be biased to return to its rest state.

A key member 507 may be fixedly attached a proximal portion of outer sheath 502. Key member 507 may overlap the proximal end of biasing member 503, and may also be fixedly attached to the proximal end of biasing member 503. Key member 507 may be slidably received in a passage 509 in a keyed member 511. Key member 507 may have an outer shape complementary to the shape of passage 509, such that torque may be transferred from keyed member 511 to key member 507.

Keyed member 511 may be received within passage 162 of handle body 158 or slot 498 of handle body 458. Keyed member 511 may be fixedly coupled to handle bodies 158 or 458 by interference fit between keyed member 511 and walls forming passage 162 or walls 496 forming slot 498. Additionally or alternatively, keyed member 511 may be fixedly coupled to walls forming passage 162 or walls 496 of slot 498 by adhesive, or any other suitable form of attachment.

In use, end effector 142 may be extended and expanded to capture object 182 by moving actuation members 146 or 446 proximally relative to handle bodies 158 or 458. This may cause components coupled to actuation members 146 or 446, such as connector 150, biasing member 503, key member 507, outer sheath 502, and support members 130, 132, and 134, to move proximally relative to components coupled to handle bodies 158 or 458, such as movable members 106, 108, and 110, drive member 104, and keyed member 511.

Once object 182 is captured within the extended and expanded end effector 142, end effector 142 may be retracted and contracted to close movable members 106, 108, and 110, and/or support members 130, 132, and 134, around object 182. To close end effector 142, actuation members 146 or 446 may be moved distally relative to handle bodies 158 or 458. This may cause components coupled to actuation members 146 or 446, such as connector 150, biasing member 503, key member 507, outer sheath 502, and support members 130, 132, and 134, to move distally relative to components coupled to handle bodies 158 or 458, such as movable members 106, 108, and 110, drive member 104, and keyed member 511.

When end effector 142 engages object 182, object 182 may obstruct further closing of end effector 142. If the user attempts to move actuation members 146 or 446 distally relative to handle bodies 158 or 458, the force exerted by the user may overcome the rest state of biasing member 503. Actuation members 146 or 445, by moving connector 505 that may be coupled to biasing member 503, may pull a distal portion of biasing member 503 distally, while outer sheath 502, and the proximal portion of biasing member 503 coupled to outer sheath 502, may remain relatively static due to object 182 preventing further closure of end effector 142 and obstructing distal movement of outer sheath 502. As such, biasing member 503 may elongate to accommodate that movement, allowing actuation members 146 or 446 to move further distally without causing distal movement of outer sheath 502 and support members 130, 132, and 134. The elongation of biasing member 503 may take up movement/forces that would otherwise be transferred to support members 130, 132, and 134 and movable members 106, 108, and 110. By taking up such forces, tearing, flaring, breaking, or other types of damage to support members 130, 132, and 134, through overly forceful contact with movable members 106, 108, and 110, may be avoided. The forces between support members 130, 132, and 134 and movable members 106, 108, and 110 may be limited such that they do not exceed what support members 130, 132, and 134 can withstand before tearing, flaring, breaking, or suffering another type of damage. Biasing member 503 may begin taking up the forces when they fall outside a predetermined range.

Alternatively, biasing member 503 may be fixedly coupled to outer sheath 502 at both the proximal and distal ends of biasing member 503. The portion of biasing member 503 distal to connector 505 may have gaps between its turns, and may act as a compression spring between connector 505 and outer sheath 502, while the portion of biasing member 503 proximal to connector 505 may act as a tension spring between connector 505 and outer sheath 502. In this arrangement, if the user attempts to move actuation members 146 or 446 distally relative to handle bodies 158 or 458 when further closing of end effector 142 is limited by the presence of object 182 therein, the compression spring portion of biasing member 503 may compress and/or the tension spring portion of biasing member 503 may elongate, allowing actuation members 146 or 446 and handle bodies 158 or 458 to move distally without moving outer sheath 502 and support members 130, 132, and 134 distally. That elongation may help prevent bringing support members 130, 132, and 134 against movable members 106, 108, and 110 with enough force to cause flaring, tearing, breaking, or other damaging of support members 130, 132, and 134. That is, the compression spring portion of biasing member 503 and/or the tension spring portion of biasing member 503 may take up excess closing forces/motions to prevent damage to support members 130, 132, and 134. Biasing member 503 may limit forces between support members 130, 132, and 134 and movable members 106, 108, and 110 so the forces remain below a tear, flare, or break strength of one or more of support members 703. Biasing member 503 may begin taking up those forces/motions when they fall outside a predetermined range depending, at least in part, on the spring constant of biasing member 503.

In use, the user may also attempt to rotate end effector 142 about the longitudinal axis of outer sheath 502 by rotating actuation members 146 or 446, handle bodies 158 or 458, and handle cover 160 about the longitudinal axis of outer sheath 502. The engagement between key member 507 and keyed member 511 may help ensure that rotation of actuation members 146 or 446, handle bodies 158 or 458, and handle cover 160 about the longitudinal axis of outer sheath 502 may result in rotation of connector 505, biasing member 503, outer sheath 502, and support members 130, 132, and 134 in unison with drive member 104 and movable members 106, 108, and 110.

FIGS. 6A and 6B show a torque transfer clip 611 that is an alternative to key member 507 and keyed member 511 (FIGS. 5A and 5B). Torque transfer clip 611 may fit by interference fit, adhesive, or any other suitable form of attachment, into passage 162 of handle body 158 or slot 498 of handle body 458. Proximal portions of biasing member 503 and outer sheath 502 may be fixedly coupled to torque transfer clip 611, within a passage 609 extending longitudinally through torque transfer clip 611, by adhesive or any other suitable attachment.

Figure 7:
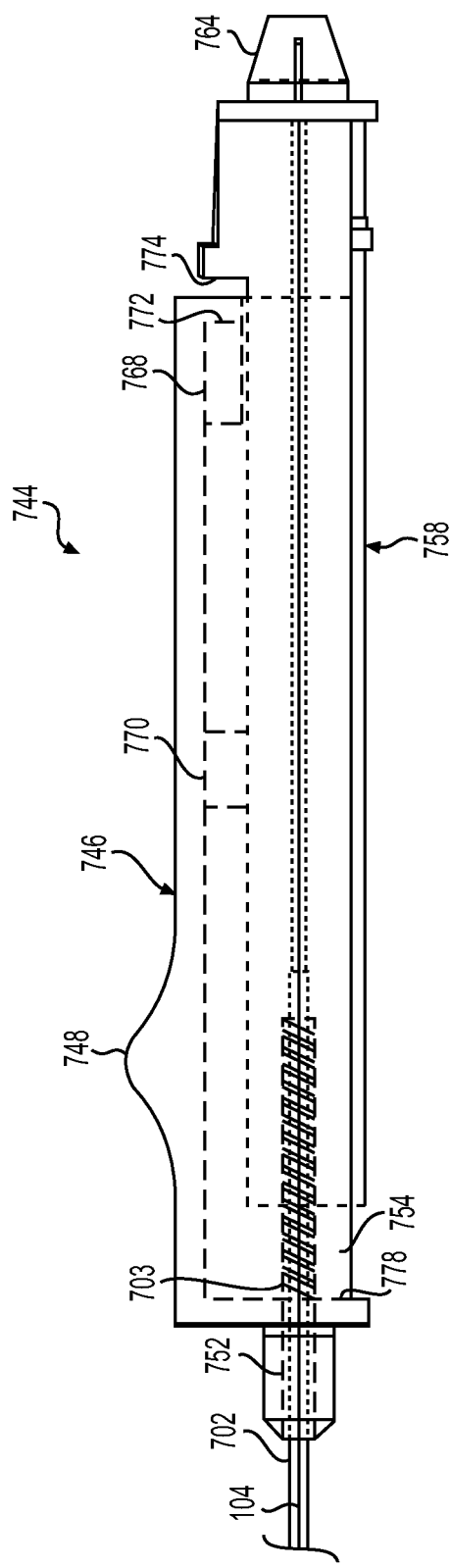
FIG. 7 is a side view of a portion of a retrieval device, in accordance with aspects of the present disclosure.

FIG. 7 shows portions of other aspects of retrieval device 100. Retrieval device may include an outer sheath 702. Drive member 104 may extend through outer sheath 702, and may be longitudinally slidable proximally and distally relative to outer sheath 702. Movable members 106, 108, and 110 may be coupled to drive member 104 (FIGS. 1B and 1D). Proximal portions of support members 130, 132, and 134 may be fixedly coupled to the distal end of outer sheath 702 by, for example, coupler 138 or any other suitable form of attachment. Movable members 106, 108, and 110, and support members 130, 132, and 134, may form end effector 142.

A handle assembly 744 may include an actuation member 746. Actuation member 746 may have a protrusion 748 on its upper surface, on which the user may exert forces on actuation member 746 using his or her thumb. A proximal portion of sheath 702 may extend through a lumen 752 of actuation member 746 and into a passage 754 of actuation member 746. Sheath 702 and actuation member 746 may slide proximally and distally relative to each other.

Drive member 104 may extend proximally through lumen 752 of actuation member 746, and through a passage 754 in actuation member 756. Drive member 104 may be coupled to a vise 764 on a proximal end of a handle body 758. Handle body 758 may slidably engage actuation member 746. For example, handle body 758 may be slidably received within passage 754 of actuation member 746, such that handle body 758 and actuation member 746 may slide proximally and distally relative to each other. Handle body 758 may be hollow. The proximal portion of sheath 702 may extend into the hollow area of handle body 758. It is contemplated that handle body 758 may be coupled to handle cover 160 and end cap 166 (FIGS. 1A and 1C). Screwing end cap 166 on handle cover 160 may help close vise 764 around the proximal end of drive member 104.

When actuation member 746 is moved distally from the position in FIG. 7 relative to handle body 758, outer sheath 702 and support members 130, 132, and 134 may move distally relative to drive member 104 and movable members 106, 108, and 110. The distally moving support members 130, 132, and 134 may slide over portions of movable members 106, 108, and 110, putting end effector 142 in its retracted and contracted state (FIG. 1B). A stroke limiter 768 coupled to a proximal portion of actuation member 746 may set a limit on distal movement of actuation member 746 when stroke limiter 768 comes into contact with a stop or abutment 770 on handle body 758. When the distal end of stroke limiter 768 contacts the proximal end of stop 770, end effector 142 may be in its fully retracted and contracted state.

With end effector 142 in a retracted and contracted state, actuation member 746 may be moved proximally relative to handle body 758, causing outer sheath 702 and support members 130, 132, and 134 to move proximally relative to drive member 104 and movable members 106, 108, and 110. Continued proximal movement of actuation member 746 may lead to increasing exposure of movable members 106, 108, and 110 from the distal ends of support members 130, 132, and 134, and extension and expansion of end effector 142 (FIG. 1D). When a stop or abutment 772 on a proximal end of actuation member 746 contacts a stop or abutment 774 on handle body 758, end effector may be at full extension and expansion.

A biasing member 703 may couple actuation member 746 and sheath 702. For example, biasing member 703 may be a coil spring surrounding a portion of outer sheath 702 within handle assembly 744. Alternatively, biasing member 703 may include an elastic tube made of silicone or rubber. A distal end of biasing member 703 may be fixedly coupled to a wall 778 of actuation member 746. A proximal end of biasing member 703 may be fixedly coupled to a proximal end portion of sheath 702. During proximal movement of actuation member 746 relative to handle body 758, biasing member 703 may remain in rest state. Biasing member 703 may provide a substantially non-moving link between actuation member 746 and outer sheath 702 during extension and expansion of end effector 142.

When end effector 142 captures object 182 (FIG. 1D), the user may attempt to close end effector 142 around object 182 by moving actuation member 746 distally relative to handle body 758. Movable members 106, 108, and 110 may at some point engage the outer surface of object 182 during closing of end effector 142. Object 182 may prevent further closure of end effector 142. Further movement of actuation member 746 distally could bring one or more of movable members 106, 108, and 110 against one or more of support members 130, 132, and 134 with sufficient force to tear, flare, break, or otherwise damage the distal ends of one or more of support members 130, 132, and 134.

Biasing member 703 may reduce the likelihood of damaging one or more of support members 130, 132, and 134 through excessive forceful engagement with one or more of movable members 106, 108, and 110. When end effector 142 closes on object 182, and object 182 obstructs further closing of end effector 142, further attempts by the user to move actuation member 746 distally relative to handle body 758 may cause biasing member 703 to elongate. That is, wall 778 of actuation member 746 may pull the distal end of biasing member 703 distally while outer sheath 702 and the proximal end of biasing member 703 remain relatively static due to object 182 obstructing distal movement of outer sheath 702 and support members 130, 132, and 134. Elongation of biasing member 703 may allow actuation member 746 to move further distally without causing distal movement of outer sheath 702 and support members 130, 132, and 134. The elongation may take up movement/forces that would otherwise be transferred to support members 130, 132, and 134 and movable members 106, 108, and 110. By taking up such forces, tearing, flaring, breaking, or other types of damage to support members 130, 132, and 134 through forceful contact with movable members 106, 108, and 110, may be avoided. For example, biasing member 703 may limit forces between support members 130, 132, and 134 and movable members 106, 108, and 110 so the forces remain below a tear, flare, or break strength of one or more of support members 703. Biasing member 703 may being taking up forces when they fall outside a predetermined range. The predetermined range may depend, at least in part, on the spring constant of biasing member 703.

Figure 8:
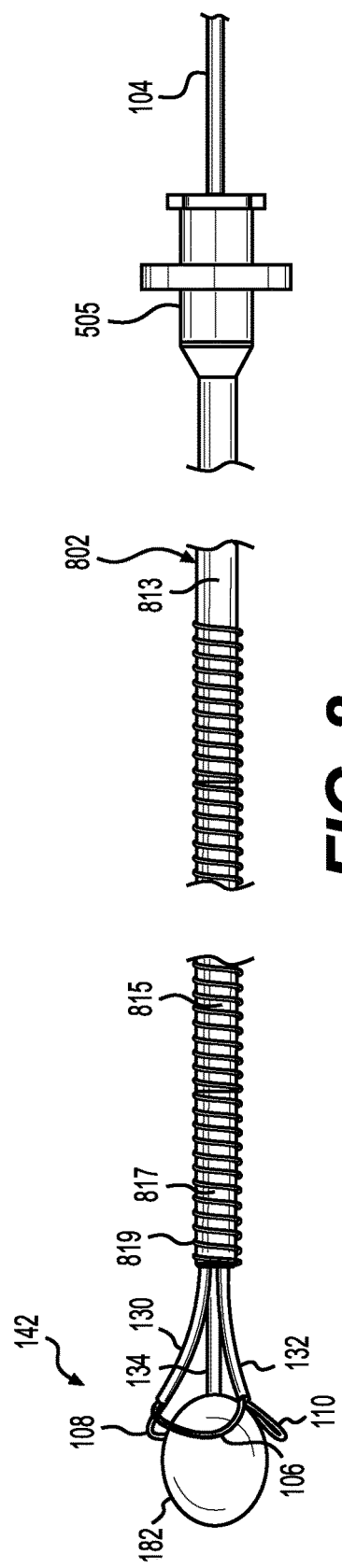
FIG. 8 is a side view of a portion of a retrieval device, in accordance with aspects of the present disclosure.

FIG. 8 shows an outer sheath 802 that is an alternative to outer sheaths 102 and 502. At its proximal end, outer sheath 802 may be coupled to connector 505. Connector 505 may be received by connector 150 (FIGS. 1A and 1C). Outer sheath 802 may include sections having different degrees of stiffness. For example, outer sheath 802 may include a proximal section 813 having a first stiffness, an intermediate section 815 having a second stiffness, and a distal section 817 having a third stiffness. The first stiffness may be greater than the second stiffness. The third stiffness may also be greater than the second stiffness. The first stiffness and third stiffness may be substantially equal. The stiffness of a section may be made higher by providing outer sheath 802 with thicker walls in that section, or lower by providing outer sheath 802 with thinner walls in that section. Additionally or alternatively, the stiffness of a section may be made higher by making outer sheath 802 out of a stiffer material in that section, or lower by making outer sheath 802 with a more flexible material in that section. Additionally or alternatively, the stiffness of a section may be made lower by etching that section.

A biasing member 819 may be applied around outer sheath 802. Biasing member 819 may be fixedly coupled at its proximal and distal ends to outer sheath 802. For example, ends of biasing member 819 may be fixedly coupled to proximal and distal sections 813 and 817. Biasing member 819 may have gaps between adjacent turns, and may act as a compression spring, tending to bias outer sheath 802 to its full length. Portions of biasing member 819 between its proximal and distal ends may slide freely along outer sheath 802. Biasing member 819 may include a coil spring made of stainless steel, spring steel, or any other suitable material. Wire forming the coil spring may have a flat, round, or any other suitable cross-sectional shape. Alternatively, biasing member 819 may include an elastic tube made of silicone, rubber, or any other suitable material.

During use, when end effector 142 has been extended and expanded around object 182, object 182 may obstruct the full closing action of end effector 142. As the user moves actuation members 146 or 446 distally relative to handle bodies 158 or 458, outer sheath 802 may be compressed due to the force exerted by object 182 on its distal end, and the force exerted by the user on its proximal end. That compressive force may cause outer sheath 802 to shorten, and may cause biasing member 819 to be compressed. When the user stops moving actuation members 146 or 446 distally, and/or when object 182 is released from end effector 142, the compressive force on outer sheath 802 may be relieved. Biasing member 819 may decompress and elongate, leading to elongation of outer sheath 802 due to biasing member 819 being fixedly coupled at its proximal end distal ends to outer sheath 802.

Figure 10:
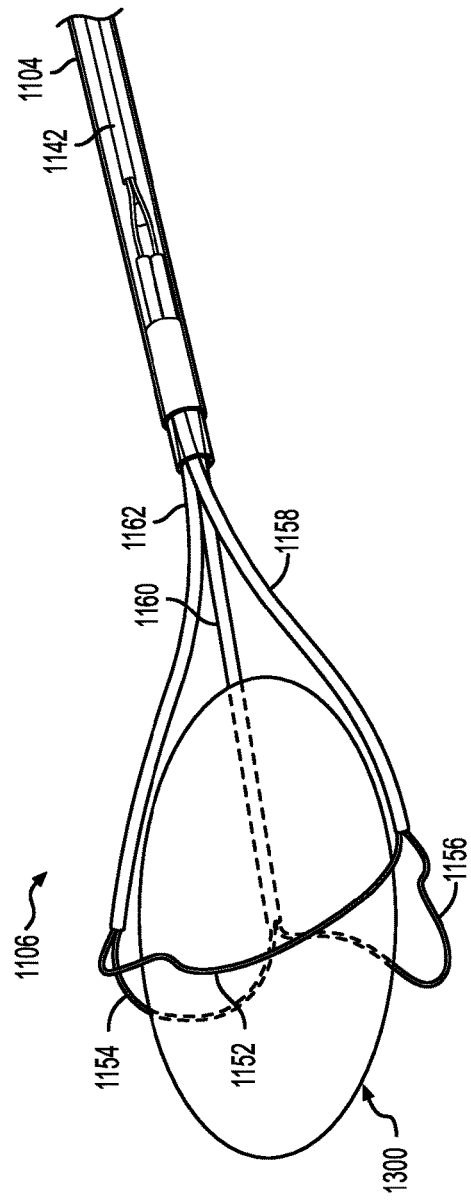
FIG. 10 is a perspective view of a distal end portion of the retrieval device of FIG. 9 in an extended state, in accordance with aspects of the present disclosure.
Figure 11:
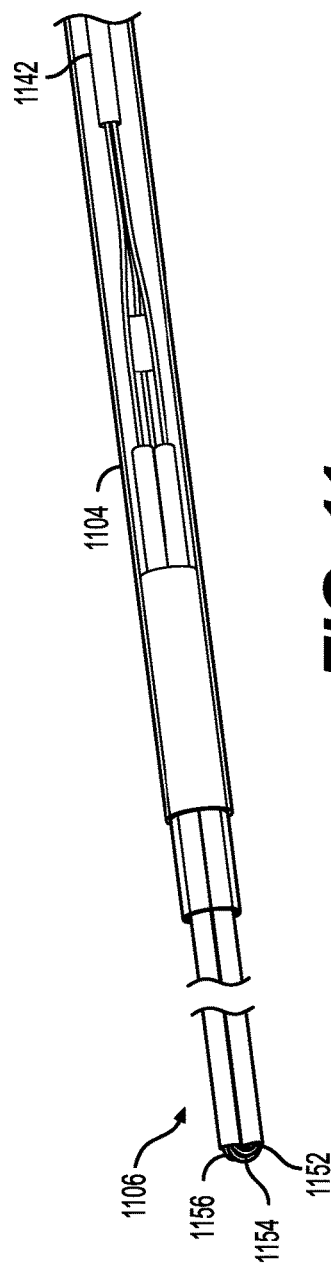
FIG. 11 is a perspective view of a distal end portion of the retrieval device of FIG. 9 in a retracted state, in accordance with aspects of the present disclosure.
Figure 12:
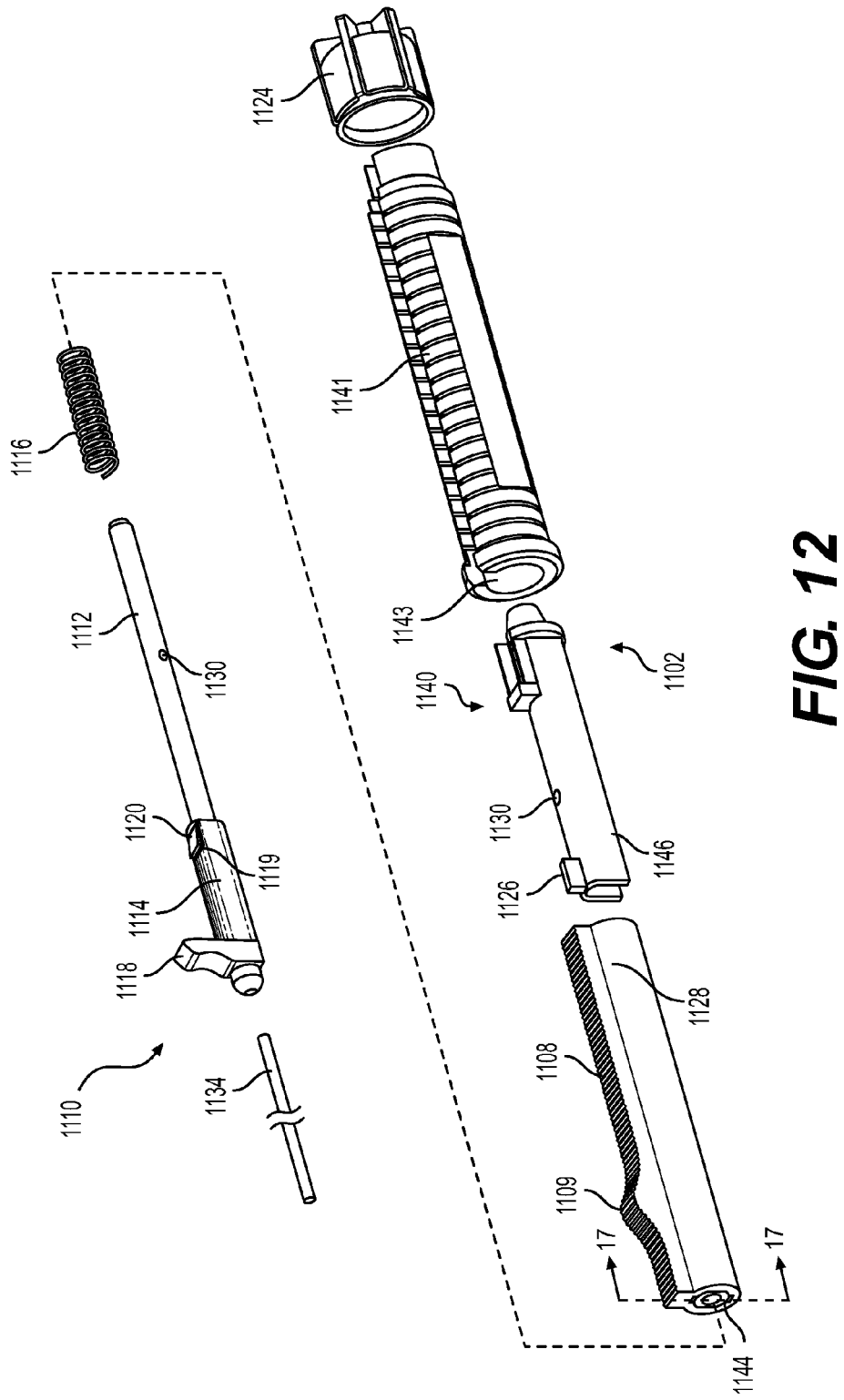
FIG. 12 is an exploded perspective view of portions of the retrieval device of FIG. 9, in accordance with aspects of the present disclosure.

FIGS. 9-17 show portions of a retrieval device 1100 according to another aspect of this disclosure. Retrieval device 1100 may include a handle assembly 1102 at the proximal end of the device 1100, a sheath 1104, and an end effector 1106 at the distal end of the device 1100. The handle assembly 1102 may include handle body 1140 (FIG. 12), a handle cover 1141, a first actuator or actuation member 1108, and a second actuator or actuation member 1110. As shown in FIG. 12, second actuator 1110 may take the form of a trigger assembly and may include various components, such as shaft 1112, plunger 1114, biasing member 1116, and trigger 1118. The second actuator 1110 reciprocates within the first actuator 1108. The first actuator 1108 controls a maximum retracted state of the device 1100 and the second actuator 1110 controls a maximum extended state of the device 1100.

Figure 9:
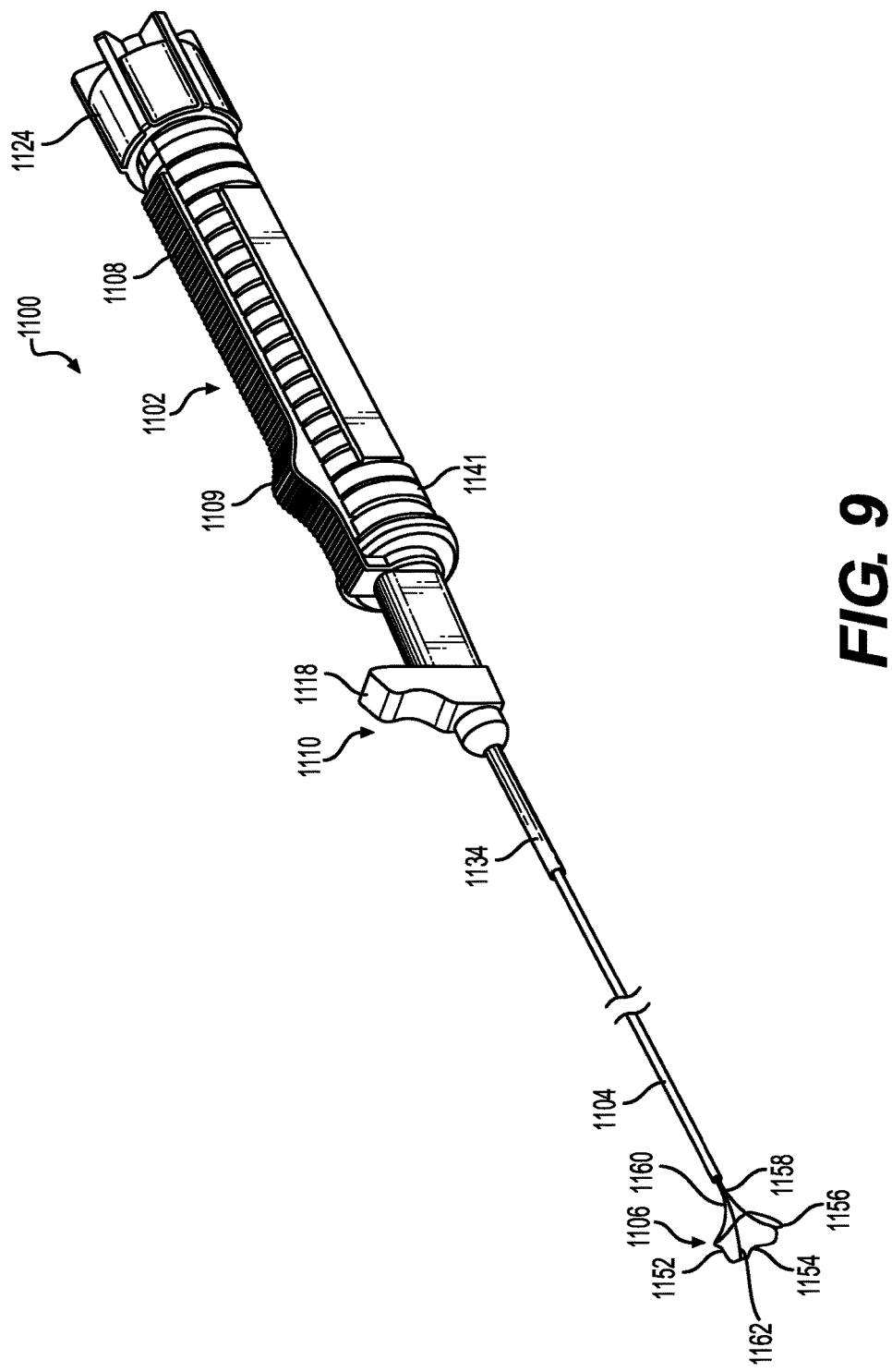
FIG. 9 is a perspective view of a portion of a retrieval device in an extended state, in accordance with aspects of the present disclosure.

Referring to FIGS. 9-11, the sheath 1104 of the device 1100 may include a longitudinally-extending lumen. Sheath 1104 may be, for example, a hollow tube and may be manufactured using of any suitable material or combination of materials. Exemplary materials may include polymers or metals. Sheath 1104 may have any suitable features, for example, sheath 1104 may have varying flexibility, therapeutic coatings, visualization features (for direct visualization and/or viewing by an imaging device), surface features (e.g. protrusions, indentations, roughened portions), shape memory properties, etc. The sheath 1104 may have any suitable size and shape for insertion in the body. Portions of the sheath 1104 may be covered by various materials such as coatings and/or covers having various suitable properties. For example, a strain relief member 1134 may be operatively coupled to the trigger assembly 1110 and may extend at least partially over a proximal portion of sheath 1104. The strain relief member 1134 may have any suitable size and shape for extending over sheath 1104 and decreasing distortion of sheath 1104 and may be manufactured using any suitable materials or combination of materials.

As shown in FIGS. 10-16, the retrieval device 1100 may also include a shaft or drive member 1142, which may extend through a lumen 1148 of the sheath 1104 and the handle assembly 1102. The drive member 1142 may be elongated, and may include, for example, one or more wires, braids, shafts, etc. configured to transfer translational and/or rotational forces from its proximal end to its distal end. Drive member 1142 may, for example, be similar to drive member 104 (FIG. 1A). As will be explained in more detail below, the sheath 1104 may be movable relative to the drive member 1142 to close and open portions of the end effector 1106.

Referring to FIGS. 9-11, the end effector 1106 may have first, second, and third movable/capture members 1152, 1154, and 1156. While three movable members are shown, one or more additional movable members may also be included. It is also contemplated that fewer than three movable members may also be included. Each of movable members 1152, 1154, and 1156 may be manufactured using any suitable material or combination of materials including, but not limited to, metals, polymers, or a combination of materials. For example, one or more of movable members 1152, 1154, and 1156 may be formed with a shape memory material, such as Nitinol, and may be treated to possess an internal bias causing one or more of movable members 1152, 1154, and 1156 to move radially outwardly away from the longitudinal axis of sheath 1104 in the absence of a constraining force.

Each of movable members 1152, 1154, and 1156 may have any suitable cross-sectional shape, including cylindrical, elliptical, polygonal, and/or irregular. One or more of the movable members 1152, 1154, and 1156 may include a portion flattened, machined, extruded, drawn, and/or etched into a different profile than a remaining portion. One or more of movable members 1152, 1154, and 1156 may be slotted to allow deflection or directional bending. Exterior surfaces of the one or more of movable members 1152, 1154, and 1156 may be roughened, notched, slotted, etched, sand-blasted, or otherwise modified to provide a better gripping surface.

Movable members 1152, 1154, and 1156 may be operatively coupled to the drive member 1142. For example, proximal ends of movable members 1152, 1154, and 1156 may be fixedly attached to a distal end of the drive member 1142 (now shown). The attachment may be provided by one or more of a splice joint, adhesives, melting, welding, crimping, joining using a heat shrinkable sleeve, and/or any other suitable attachment mechanism or process. Movable members 1152, 1154, and 1156 may, for example, be similar to movable members 106, 108, and 110.

End effector 1106 also may include first, second, and third support members 1158, 1160, and 1162. Each of the support members 1158, 1160, and 1162 may include a lumen (not shown) extending longitudinally therethrough. For example, support members 1158, 1160, and 1162 may be a hollow tube. Support members 1158, 1160, and 1162 may be disposed circumferentially about the longitudinal axis of the sheath 1104. Longitudinal axes of support members 1158, 1160, and 1162 may be disposed at equal intervals circumferentially about the longitudinal axis of sheath 1104. Any other suitable number of support members and spacing configurations may alternatively be utilized.

Each support member 1158, 1160, and 1162 may have any suitable cross-sectional shape, including cylindrical elliptical, polygonal, and/or irregular. One or more of support members 1158, 1160, and 1162 may include a portion flattened, machined, extruded, drawn, and/or etched into a different profile than a remaining portion. Support members 1158, 1160, and 1162 may be made of a flexible material, so that they may bend when being inserted into and through tortuous passages in a subject's anatomy. One or more of support members 1158, 1160, and 1162 may be slotted to allow deflection or directional bending. Exterior surfaces of one or more of support members 1158, 1160, and 1162 may be roughened, notched, slotted, etched, sand-blasted, or otherwise modified to provide a better gripping surface.

Support members 1158, 1160, and 1162 may be made of any suitable material, or combination of materials such as polymers (e.g. polyimide, or polyethylene terephthalate), and or metals (e.g. Nitinol), etc.

As shown in FIGS. 10 and 11, proximal portions of support members 1158, 1160, and 1162 are received in a distal end of sheath 1104. For example, proximal portions of one or more of support members 1158, 1160, and 1162 may be covered by a distal portion of sheath 1104, leaving a distal length exposed from the distal end of sheath 1104. Proximal portions of support members 1158, 1160, and 1162 may be fixed relative to sheath 1104. For example, via a sleeve or heat-shrinkable sleeve and/or adhesive, such as an ultraviolet light curable adhesive or cyanoacrylate. The proximal ends of support members 1158, 1160, and 1162 may be stationary relative to the distal end of sheath 1104, while allowing distal portions of the support members 1158, 1160, and 1162 to move relative to the distal end of sheath 1104 and relative to one another between the exemplary portions shown in FIGS. 10 and 11.

Each support member 1158, 1160, and 1162 may contact the other two support members. For example, each of the proximal portions of the support members 1158, 1160, and 1162 may contact the proximal portions of the other two support members, such that support members 1158, 1160, and 1162 may have a triangular arrangement around the longitudinal axis of sheath 1104. Longitudinal axes of support members 1158, 1160, and 1162 may form vertices of a triangle, and portions of the longitudinal axes may be parallel. Distal portions of support members 1158, 1160, and 1162 may be movable towards and away from the longitudinal axis of sheath 1104. The number of support members 1158, 1160, and 1162 may be equal to the number of movable members 1152, 1154, and 1156. It is contemplated that the number of support members and movable members may vary based on the type of procedure being performed. It is also contemplated that support member 1158, 1160, and 1162 may be similar to support members 130, 132, and 134.

Each of movable members 1152, 1154, and 1156 may extend distally from drive member 1142, and may enter a lumen of one of support members 1158, 1160, and 1162 at its proximal end. Each of movable members 1152, 1154, and 1156 may extend distally through the lumen of the support member, and may exit the lumen at the distal end of one of support members 1158, 1160, and 1162. Each of movable members 1152, 1154, and 1156 may then transition into a bend and may enter a lumen through the distal end of another one of support members 1158, 1160, and 1162. Each of movable members 1152, 1154, and 1156 may then extend proximally through the lumen, and may exit the lumen at the proximal end of one of support members 1158, 1160, and 1162. After exiting, each of movable members 1152, 1154, and 1156 may be operatively coupled together in any fashion, such as by a clamp, adhesive, melting, welding, friction fit, heat-shrinking, and/or any other suitable form of attachment. The movable members 1152, 1154, and 1156 are secured to allow for longitudinal movement within all of the support members 1158, 1160, and 1162. For example, during initial opening of the end effector 1106, the movable members 1152, 1154, and 1156 may all move an initial distance within the support members 1158, 1160, and 1162 to relieve opening forces of the device. The initial distance may be any suitable predetermined distance that may be controlled by the placement of a stop.

Portions of movable members 1152, 1154, and 1156 extending distally from drive member 1142 may extend alongside surfaces of a spacer to space those portions of movable members 1152, 1154, and 1156 apart from the longitudinal axis of sheath 1104, to help guide movable members 1152, 1154, and 1156 into the lumens of support members 1158, 1160, and 1162.

Movable members 1152, 1154, and 1156, and support members 1158, 1160, and 1162, form the end effector 1106. End effector 1106 may form a basket or grasper having front and side openings for capturing target objects 1300 in an open or extended state as shown in FIG. 10. In FIG. 11, end effector 1106 is shown in a retracted or closed state. End effector 1106 may be moved into its retracted or closed state by moving first actuator 1108 in a distal direction indicated by arrow "C" (shown in FIG. 13) to in turn move the sheath 1104 and associated support members 1158, 1160, and 1162 distally relative to the movable members 1152, 1154, and 1156 and drive member 1142. Moving the support members 1158, 1160, and 1162 over the movable members serves to close the end effector 1106.

In the retracted state, bends formed in the movable members 1152, 1154, and 1156 may be at or adjacent to distal ends of support members 1158, 1160, and 1162, as shown in FIG. 11. Longitudinal axes of support members 1158, 1160, and 1162 may be substantially parallel in the retracted state, and both proximal and distal portions of each of support members 1158, 1160, and 1162 may be in contact with the other support members. Portions of movable members 1152, 1154, and 1156 in the lumens of support members 1158, 1160, and 1162 may be substantially parallel. Support members 1158, 1160, and 1162, and/or sheath 1104 may counteract the inherent bias in movable members 1152, 1154, and 1156, keeping portions of movable members 1152, 1154, and 1156 from bending radially outwardly from the longitudinal axis of sheath 1104 in the retracted state.

In FIG. 13, end effector 1106 is shown in an extended state. In the extended state, portions of movable members 1152, 1154, and 1156 may be exposed from the distal ends of the support members 1158, 1160, and 1162 due to withdrawal of the sheath 1104 in a proximal direction indicated by the arrow "O". This may be accomplished by movement of the first actuator or actuation member 1108 in a proximal direction indicated by arrow "O" which may in turn move trigger assembly 1110 proximally to move or withdraw the sheath 1104 and connected support members 1158, 1160, and 1162 in a proximal direction. Once exposed, movable members 1152, 1154, and 1156 may move radially outwardly from the longitudinal axis of sheath 1104 due to inherent radially outward biasing in movable members 1152, 1154, and 1156. Radially outward movement of movable members 1152, 1154, and 1156 may cause a radially outward movement of support members 1158, 1160, and 1162. Alternatively, support members 1158, 1160, and 1162 may be biased radially outwardly, and movable members 1152, 1154, and 1156 may urge support members 1158, 1160, and 1162 into the retracted and contracted state. Sheath 1104 and support members 1158, 1160, and 1162 may be moved proximally relative to movable members 1152, 1154, and 1156 to extend end effector 1106, allowing end effector 1106 to move to its extended state.

As best shown in the exploded view in FIG. 12, the first actuator or actuation member 1108 may have a protrusion 1109 on its upper surface, on which the user may exert forces using his or her thumb to move the first actuator 1108 proximally to transition the end effector 1106 to a fully open or partially open state and distally to a fully retracted, partially retracted, or a further retracted state. The first actuator 1108 may have a generally "U" shape having a lumen therethrough, and may be slidably disposed within the handle cover 1141 having a slot 1143 through which the actuation member protrusion 1109 may extend. The first actuator or actuation member 1108 also may include a stroke limiter 1128 (FIG. 13). The stroke limiter 1128 may be a separated component such as a tube or may be formed on the first actuator 1108. The handle cover 1141 may have various surface features to help the user hold the device 1100.

Figure 17:
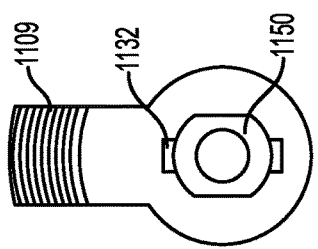
FIG. 17 is front view of a first actuator of the retrieval device along lines 17-17 of FIG. 12, in accordance with aspects of the present disclosure.

A locator body 1146 may be disposed in a portion of the first actuator 1108 lumen and may be operatively coupled to or formed within the handle body 1140. The locator body 1146 may have one or more protrusions or stops for controlling the longitudinal movement of the first actuator 1108. For example, the locator body 1146 may limit the sliding distance of the first actuator 1108 by a distal stop 1126 or proximal stop 1147. The first actuator 1108 may include a distal face 1144 to operatively couple to portions of the trigger assembly 1110. For example, FIG. 17 shows a front view of the first actuator 1108 having a keyed front hole 1150 to receive the trigger assembly 1110.

The proximal end of the locator body 1146 may include a vise 1122 or any other suitable holding mechanism for holding drive member 1142. When vise 1122 closes, drive member 1142 may be fixedly coupled. An end cap 1124 may be placed onto the proximal end of the handle assembly 1102 in any suitable manner (e.g. fasteners, adhesive, molding) to help close/clamp the vise around drive member 1142. For example, the handle assembly 1102 may include an externally threaded portion (not shown), and end cap 1124 may include complementary internal threading (not shown), so that end cap 1124 may be screwed onto handle assembly 1102.

The exterior surfaces of the locator body 1146 may have any suitable size and shape and may correspond for disposal into lumen of the first actuator 1108 having corresponding slots or grooves.

The trigger assembly 1110 may be fixedly coupled to a proximal portion of the sheath 1104 in any suitable manner, such as fasteners, snap fasteners, insert molding, heat shrink, adhesive, weld, etc. For example, the plunger 1114 may be insert molded on the sheath 1104. The trigger assembly 1110 may be operatively coupled to the first actuator 1108 in any suitable manner. For example, as shown in FIGS. 12-16, the trigger assembly 1110 may include flexing tabs or flexing tabs 1120, which may engage an interior surface of the first actuator 1108. The flexing tabs 1120 may be formed on the outer surface of the plunger 1114 and may snap into corresponding slots. In other embodiments, the flexing tabs 1120 may be replaced by keyed tabs, fasteners, screws, or any other suitable couplings that allow limited two-way movement of the plunger 1114 relative to first actuator 1108. The drive member 1142 may extend proximally through the sheath 1104 and a lumen of the trigger assembly 1110, and the lumen 150 in the first actuator 1108, and may be operatively coupled to the handle assembly 1102 at vise 1122.

In some embodiments, the trigger assembly 1110 may be operatively coupled to the first actuator 1108 by a set screw and slot coupling (not shown). In this embodiment, one or more screw holes may be formed in a distal portion of the first actuator 1108, and a portion of the plunger 1114 may include matching slots for each screw hole. Screws may be threaded into the screw holes to be aligned and extended into the slots in the plunger 1114. The screw may limit the sliding distance of the plunger 1114. The limit of longitudinal movement of the plunger 1114 may be limited to the abutment of the screw to each end of the slot in the plunger 1114.

The biasing member 1116, such as a spring, may be disposed over a portion of the shaft 1112 of the trigger assembly 1110. The trigger 1118 of the trigger assembly 1110 may extend from the plunger 1114. A user may exert forces on the trigger 1118 of the trigger assembly 1110 using his or her thumb or index finger. Any suitable materials or combination of materials having any suitable properties may be used to form the components of the handle assembly 1102. For example, metals or polymers. The plunger 1114 and shaft 1112 may have any suitable size and shape. For example, the plunger 1114 may have flat, planar exterior surfaces for keyed coupling with the first actuator 1108, and the shaft 1112 may have a round tubular shape over which biasing member 1116, such as a spring, may be disposed.

FIG. 12 shows partially unassembled portions of device 1100 in which cap 1124 may be used to join the handle cover 1141, the drive member 1142, and locator body 1146 together. To assemble, the drive member 1142 may be placed and located between portions of the vise 1122. The handle cover 1141 may be slid over the internal parts (e.g. first actuator 1108 and locator body 1146) of the handle assembly 1102. The cap 1124 when tightened onto the handle cover and about the vise 1122, may compress the vise 1122, locking the drive member 1142, locator body 1146, handle cover 1141, and cap 1124 together allowing the first actuator 1108 to slide relative to the locator body 1146.

As noted above, the internal components of the handle assembly 1102 may be assembled by inserting the stroke limiter 1128 of a particular length for a particular size end effector 1106 in the first actuator 1108. The stop 1126 of the locator body 1146 may be aligned with the first actuator 1108 and the locator body 1146 may be disposed into the first actuator 1108. Prior to insertion into the handle body 1140, the plunger 1114 may be fixed to the sheath 1104 in any suitable manner, for example, insert molded, or glued. The biasing member 1116 may be positioned on to the shaft 1112 of the trigger assembly 1110, and the trigger assembly may be inserted into the keyed front hole 1150 of the first actuator 1108. The keyed hole 1150 may have any suitable shape and size that may limit rotational movement of the plunger 1114 about the first actuator 1108 and to allow torque transfer from the handle assembly 1102 to the sheath 1104. The plunger 1114 may have a shape that corresponds to the keyed front hole 1150 of the first actuator 1108. The shaft 1112 may be inserted and aligned through the front keyed hole 1150 and extended through a mid-hole 1130 of the first actuator 1108, as shown in FIG. 13. The drive member 1142 may be disposed in the vise 1122. The flexing tabs 1120 may be aligned to the keyed front hole 1150 and may snap into place. The drive member 1142 may be trimmed to a suitable length so that the cap 1124 can be assembled at final assembly of the device 1100.

The plunger 1114 may move a distance shown in FIG. 13 and FIG. 14. The user may use his or her thumb to move the plunger 1114 in one direction via the trigger 1118 and the biasing member 1116 may return the plunger 1114 back in the opposite direction. As the sheath 1104 is directly fixed to the plunger 1114, changing the length of the plunger 1114 relative to the first actuator 1108 moves the length of the sheath 1104 relative to the first actuator 1108, which in turn moves the end effector 1106.

As described above, the device 1100 may be used to retrieve a target object, such as organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. The device 1100 may be used for single hand use while the other hand may be used to manipulate another portion of the device 1100 or another device, such as an ureterscope. In this manner, using the trigger 1118 and the first actuator 1108, the user may manipulate and maneuver both the device 1100 and any other device (e.g. a scope) without the aid of an assistant. The user may use the two actuators—the first actuator or actuation member 1108 and the second actuator or trigger assembly 1110 to manipulate the retraction and/or extension of the sheath 1104 relative to the movable members 1152, 1154, and 1156 to open and close the end effector 1106.

As shown in FIG. 10 the end effector 1106 may be extended or opened to capture the target object 1300. In order to accomplish this, the actuation member protrusion 1109 may be gripped and the first actuator 1108 may be moved proximally relative to the handle body 1140 and the drive member 1142 along the locator body 1146 and shaft 1112. In an extended or open state as shown in FIG. 13, a proximal end of the first actuator 1108 may abut with a proximal protrusion of the locator body 1146. As first actuator 1108 moves proximally, the sheath 1104 may withdraw proximally to expose the movable members 1152, 1154, and 1156 allowing the end effector 1106 to expand or open. This proximal movement is accomplished by the abutting connection of the proximal end of the plunger 1114 to the first actuator 1108 by flexing tabs 1120, and the connection of the distal end of the plunger 1114 to the sheath 1104.

As shown in FIG. 14, the trigger assembly 1110 may be used to further extend or open the end effector 1106. The trigger 1118 may be actuated to move the trigger assembly 1110 in the proximal direction. The trigger 1118 may be operated with the index finger or the thumb to pull the trigger 1118 proximally. Proximal movement of the trigger 1118 may compress the biasing member 1116 and further withdraw the sheath 1104 proximally an additional distance to further extend or open the end effector 1106 beyond its normal operating range (diameter) for the purposes of capturing a larger target through its front opening, releasing a stuck target object, or to enlarge the side opening of the end effector 1106 to allow larger side opening target object capture. Upon release of the trigger 1118, the biasing member 1116 may return the plunger 1114 back to its original stroke length (FIG. 13). The change in the length of the biasing member 1116 may be equal to the movement of the sheath 1104 relative to the first actuator 1108.

FIG. 15 shows the end effector 1106 in a standard or fully closed or retracted state. The retracted state may be accomplished by moving the first actuator 1108 distally a distance having a stroke length "S" starting at a position S1 (corresponding to a distal end of the stroke limiter 1128) and moving to a position near stop 1126. The actuation member protrusion 1109 may be gripped and the first actuator 1108 may be moved distally relative to the handle body 1140 and the drive member 1142 along the locator body 1146 and shaft 1112. In a retracted state as shown in FIG. 15, the sheath 1104 may be urged over the movable members 1152, 1154, and 1156 to retract the end effector 1106.

FIG. 16 shows the end effector in a further retracted state in which the first actuator 1108 may be further pushed in a distal direction an additional stroke length "A" for a total stroke length "T" from the fully retracted state shown in FIG. 15 at which the stroke limiter 1128 travel from position S1 to a position abutting stop 1126 to maintain retraction of the end effector 1106. This state may be advantageous, for example, when the device 1100 is traversing a tortuous path in the body, and the end effector 1106 may require the assistance of the biasing member 1116 to maintain the end effector 1106 in a closed or retracted state. In this further retracted state, the standard stroke length "S" may be increased by an additional "A" closure length. The additional closure length "A" may assure sufficient sheath 1104 length to slide over the end effector 1106 and may provide tactile confirmation that the end effector 1106 is fully retracted. Any movement of 108 beyond the maximum distal movement of sheath 1104 (as defined by the movable members limiting movement of the support members distally), may result in displacement of the biasing member 1116 to cause the biasing member 1116 to compress. In turn, the compression of the biasing member 1116 controls the stresses at the end effector 1106 in the closed position, in that the spring force replaces the force applied to the first actuator or actuation member 1108. As the first actuator 1108 is released, the biasing member 1116 may return the flexing tabs 1120 back to the back side of the first actuator 1108, and the sheath 1104 to an extended length as shown in FIG. 15. Thus, the biasing member 1116 allows for a lost motion connection between the first actuator 1108 and the second actuator 116. In addition, the first actuator 1108 may transfer a force to the biasing member 1116 when the first actuator 1108 moves in the distal direction. The biasing member 1116 is configured to reduce the force, and transfer the reduced force to the sheath 1104, when the force on the first actuator 1108 exceeds a predetermined value. As the first actuator 1108 moves distally relative to the handle body 1140, the additional distance A beyond the first distance S, the biasing member 1116 compresses as the first actuator 1108 moves the additional distance A.

For example, as the sheath 1104 is restricted from moving in the distal direction by the bends of the movable member 1152, 1154, and 1156 for closure, the continued movement of the first actuator 1108 in the distal direction compresses the biasing member 1116 a predetermined distance "x" against the plunger 1114. The force that the compressed biasing member 1116 exerts on the plunger 1114 which, is connected directly to the sheath 1104 is in accordance with Hooke's law $F=Kx$ discussed above, where K is the spring constant and x is equal to the additional distance A shown in FIG. 15. Since the biasing member 1116 is compressed initially during the assembly of the plunger 1114 to the first actuator 1108, $F=Kx$, where $x=A+x$, where $x_1$=the free length of the biasing member 1116—the initial compressed length of the biasing member 1116. The force exerted by the biasing member 1116 on the sheath 1104 and support tubes 1158, 1160, and 1162 at the end of stroke distance A is greater than the stroke distance S, since the change of the length of the biasing member 1116 is greater at the end of stroke A. At the end of stroke S, the biasing member 1116 may be biasing the plunger 1114 against the first actuator 1108, thus and no spring force may be exerted to the sheath 1104. The closed or retracted state shown in FIG. 15 in which the first actuator 1108 moves a stroke distance S to completely close the end effector 1106 and further movement of the first actuator 1108 the additional stroke distance A may provide an additional closure force.

The biasing member 1116 may have any suitable properties according to Hooke's law. For example, the biasing member 1116 may have any suitable spring constant K, such as between 0.700 lb./in and 0.900 lb./in. In some embodiments, the biasing member 1116 may have a K value of about 0.872 lb./in. The biasing member 1116 may have any suitable load height, for example, an initial load height of about 1.130" producing an initial spring force of about 0.104 lbf (0.047 kgf). The biasing member 1116 may have any suitable expansion force such as no more than about 0.7 lbf (0.32 kgf) when the biasing member 1116 is compressed about 18 mm to force the plunger 1114 to extend distally and to return the length of the sheath 1104 to its initial length. A force of about 0.25 lbf (0.11 kgf) may be of sufficient force to advance the sheath 1104 over the drive member 1142 further compressing the biasing member 1116 to advance the sheath 1104 to close the end effector 1106 when the first actuator 1108 is moved in the distal direction. In one embodiment, the size of the end effector 1106 may be between 30 to about 70% larger in the release state shown in FIG. 14 than in the extended state shown in FIG. 13. For example, the maximum standard open size of the end effector 1106 in the extended state (FIG. 13) may be about 8 mm in diameter and the trigger assembly 1110 may further extend the open size to about 15 mm in the release state (FIG. 14). The biasing member 1116 provides a neutral bias to the first actuator 1108 when the end effector 1106 is in the extended state shown in FIG. 13.

The device 1100 also may provide stroke relief when the device is actuated. For example, distal movement of sheath 1104 coupled to the plunger 1114 may be restricted when the device is in the closed or retracted position with the end effector 1106 is empty, or when the end effector 1106 is holding an object. Movement of the first actuator 1108 in the distal direction when the sheath is retracted will compress the biasing member 1116 a predetermined distance against the plunger 1114. The force that the compressed biasing member 1116 exerts on the plunger 1114, which is fixed to the sheath 1104 is F=Kx (Hooke's law), where K is the spring constant and x is equal to the change in the length of the biasing member 1116 delta x, since the biasing member 1116 may be initially compressed during assembly of the plunger 1114 to the first actuator 1108. Then F=Kx where x equal delta $x+x_1$ where $x_1$=(free length of the biasing member 1116)—(the initial compressed length of the biasing member 1116). The force exerted by the compressed biasing member 1116 on the sheath 1104 and support tubes 1158, 1160, and 1162 may be less than the force applied directly by the first actuator 1108 if the biasing member 1116 were not present, thus relieving or controlling the stroke force. The biasing member 1116 may have any suitable K constant.

In one embodiment, a target object may be captured by opening the end effector 1106 to its open diameter in the extended state (FIG. 13) and advancing the front opening of the end effector 1106 towards the target object, capturing the object, moving the target object to a desired location. Actuating trigger assembly 1110 may be moved proximally to further open the end effector 1106 to the further extended or release state (FIG. 14), to grab or capture larger target objects. The trigger assembly 1110 also may be advantageously used to open the end effector 1106 during release of the object so that the end effector 1106 may open to a larger size than the end effector 1106 during capture of the target object. Thus, the trigger assembly 1110 may be activated when the release state is needed or when a target object is stuck in the effector 1106.

Additionally or alternatively, and referring to FIGS. 9-17, the biasing member 1116, when assembled in handle assembly 1102, may be compressed between the plunger 1114 and a portion of the first actuator 1108. For example, the biasing member 1116 may be compressed between the plunger 1114 and a rib, wall, or protrusion on an underside of the first actuator 1108 (FIGS. 13-16). The biasing member 1116 may be compressed to an initial length from an equilibrium length to bias the first actuator 1108 relative to the sheath 1104 with a restoring force. The biasing member 1116, when not compressed or tensioned, may be in its equilibrium length, where a change in length of the biasing member 1116 is near or equal to zero, resulting in the restoring force exerted by the biasing member 1116 to be near or equal to zero. The compressed initial length of the biasing member 1116, however, may exert a restoring force on a proximal end portion of the plunger 1114 and/or the rib of the first actuator 1108, thereby extending and maintaining the sheath 1104 in a position, with portions of the sheath 1104 at a distance from the first actuator 1108, during operation of the end effector 1106.

The initial restoring force may correspond to the compressed initial length, and may be calculated using Hooke's law. For example, the initial restoring force "$F_1$" exerted on the sheath 1104 and support members 1158, 1160, and 1162 by the biasing member 1116, when the biasing member 1116 is at its compressed initial length, can be calculated using the equation $F_1=-Kx_{01}$, where $F_1$ is a resulting force vector (e.g., a magnitude and direction of the restoring force the biasing member 1116 exerts on the sheath 1104 via the plunger 1114 and also is the restoring force the biasing member 1116 exerts on the first actuator 1108); k is a rate, spring constant, or force constant of the biasing member 1116, which may depend on material and construction of biasing member 1116; the negative sign may indicate that the force the biasing member 1116 exerts is in a direction opposite from its displacement; and $x_{01}$ is a displacement vector (e.g., a distance and direction the biasing member 1116 may be deformed from its equilibrium length or free length to its initial length).

Referring to FIGS. 9-11, the sheath 1104 and attached support members 1158, 1160, and 1162 may retract relative to the drive member 1142 when the initial restoring force exerted by the biasing member 1116 is overcome by another force, such as friction or drag. Put another way, the initial restoring force may be used to maintain a substantially constant working length of the sheath 1104 relative to the first actuator 1108. In turn, the support members 1158, 1160, and 1162 may cover and/or retract a consistent length relative to the movable members 1152, 1154, and 1156 to fully close the end effector 1106 and/or to fully open the end effector 1106 to a consistent size.

The size of the end effector 1106 may be expressed in terms of lengths of the movable members 1152, 1154, and 1156 that may be extended and retracted from the tips of the support members 1158, 1160, and 1162 to form a perimeter of the distal loop of the end effector 1106. The lengths or amounts of the movable members 1152, 1154, and 1156 extended from the end of each of the support members 1158, 1160, and 1162 may be governed by the stroke length of the first actuator 1108, and/or may be equated to a maximum stone dimension or that can fit in the perimeter of the front loop of the end effector 1106.

The initial restoring force at the initial length of the biasing member 1116 may be selected so as to be greater than a friction force that may be encountered between the assembly of the movable members 1152, 1154, and 1156 and the drive member 1142, and the assembly of the sheath 1104 and the support members 1158, 1160, and 1162 when they are operated in a tortuous path. This initial restoring force setting may enable the sheath 1104 to maintain its working length, and overcome drag to enable the end effector 1106 to fully expand, extend, contract, and/or retract.

As stated above, the initial restoring force may maintain the working length of the sheath 1104 during expansion and contraction of the end effector 1106, brought about by proximal and distal strokes of the first actuator 1108, when there is no stone present. The same strokes of the first actuator 1108 may be used to capture a stone. The maximum stress and strain applied to components of the retrieval device 1100 by the restoring force of the biasing member 1116, may occur after a distal stroke of the first actuator 1108 that puts the end effector 1106 in a fully contracted and retracted state.

The amount of stress and strain that may be applied to the components of the retrieval device 1100 may be limited or otherwise managed. This may be accomplished using the biasing member 1116, which may include a coil spring, by selecting or setting a maximum restoring force of the biasing member 1116. For example, the maximum restoring force may be below the material strength of components of retrieval device 1100 that can be damaged during a distal stroke of the first actuator 1108.

The maximum restoring force generated by a user's hand may be a function of the maximum stone size that can be captured in the front loop of the end effector 1106. A stone's perimeter may be used to approximate the stone's cross-section that is captured by the front loop. Limiting the size of the front loop, more specifically the perimeter of the front loop that is formed when the end effector 1106 is in the expanded state, will limit the size of stone that can be captured only to those stones with an equal to or smaller perimeter than the front loop. By limiting the maximum stone size that can be captured, the maximum restoring force that can be applied by the restoring force of the biasing member 1116 to the components of the retrieval device 1100 may be limited.

When capturing a stone, one scenario may involve the user opening the end effector 1106 to its maximum front loop perimeter with the first actuator 1108, by sliding the first actuator 1108 with a full proximal stroke, whereby the end effector 1106 may be fully expanded and extended (FIG. 13). The user may position and engage the front loop perimeter over the perimeter of the stone to be captured. The user may then start to slide the first actuator 1108 in the distal direction with a distal stroke, causing the end effector 1106 to move to its contracted and retracted state, and closing the end effector 1106 about the stone. At a point of the distal stroke, the stone's perimeter may begin to prevent the front loop from closing all the way to a fully contracted state. This may cause resistance between the assembly of the sheath 1104 and support members 1158, 1160, and 1162, and the assembly of the movable members 1152, 1154, and 1156 and the drive member 1142, preventing the support members 1158, 1160, and 1162 from sliding over the movable members 1152, 1154, and 1156. When the resistance force becomes equal to or greater than the initial restoring force $F_1$ at the initial length of biasing member 1116, further sliding of the first actuator 1108 in the distal direction may start to compress the biasing member 1116 to a loaded length (FIG. 14), increasing its restoring force, and tightening the front loop about the stone. The maximum restoring force and the maximum tightness of the front loop about the stone, may be reached at the end of the distal stroke of the first actuator 1108.

The maximum stress and strain applied to one or more of the components of the retrieval device 1100, such as to the support members 1158, 1160, and 1162, sheath 1104, movable members 1152, 1154, and 1156, and/or drive member 1142, may occur when the first actuator 1108 is actuated with a distal stroke to its position that corresponds to the end effector 1106 being fully contracted and retracted, with a stone of maximum size captured within the end effector 1106 front loop. This maximum restoring force may also be the maximum force that the hand may apply via the first actuator 1108. Put another way, the hand may apply a force via the first actuator 1108 substantially equal to the restoring force of the biasing member 1116, the magnitude of the restoring force being a function of the size of the stone's perimeter that is engaged with the front loop of the end effector 1106. It should be noted that the restoring force acting on the sheath 1104 and the end of the plunger 1114 may also be the restoring force of the biasing member 1116 that is acting on the first actuator 1108.

A change in the length ($X_{O2}$) of the biasing member 1116 when the biasing member 1116 is placed under a load, or the change in the compression of the biasing member 1116 from the equilibrium length when placed under a load, may be a function of the size of the stone being capture, and more specifically, a function of the size of the perimeter of the stone about which the front loop of the end effector 1106 conforms and tightens. Initial closure of the end effector 1106 by the advancement of the first actuator 1108 may close the front loop about the surface of the stone. The perimeter of the stone is approximated by the perimeter of the front loop. Further closure of the end effector 1106 against the stone by the advancement of the first actuator 1108 may cause sufficient resistance of the support members 1158, 1160, and 1162 from advancing over one or more exposed portions of movable members 1152, 1154, and 1156, causing the biasing member 1116 to compress or change its length. The change in length ($X_{O2}$) may be approximately ⅓ of the perimeter of the stone that is captured by or within the front loop, since there are three movable members 1152, 1154, and 1156 that extend equally to form the front loop.

For the simplicity of perimeter calculations described below, a stone having a circular cross section (e.g., a spherical or cylindrical stone) is used. The change in length $X_{O2}$ can be approximated by the circumference of the stone divided by 3, or $(\pi*d)/3$, where d is a diameter of the stone. However, one of ordinary skill would appreciate that stones may have irregular shapes, and that the calculations described herein may be adjusted based on the particular stone shape.

A restoring force "$F_2$" may be exerted on the components of retrieval device 1100, such as the sheath 1104 and/or support members 1158, 1160, and 1162 by the biasing member 1116 as the first actuator 1108 is moved. $F_2$ may also be the force that is exerted on the first actuator 1108 by the biasing member 1116. The restoring force "$F_2$" may be the same in magnitude for two different stones when the stones' perimeters are equal on length.

The restoring force $F_2$ can be calculated using Hooke's Law, where $F_2 = -KX_{O2}$, wherein: $F_2$=the resulting force vector–the magnitude and direction of the restoring force the biasing member 1116 exerts on the sheath 1104 via the plunger 1114 with distal movement of the first actuator 1108, and also the restoring force the biasing member 1116 exerts on the first actuator 1108; K=the rate, spring constant, or force constant of the biasing member 1116, a constant that depends on the biasing member's material and construction, wherein the negative sign indicates that the force the biasing member 1116 exerts is in the opposite direction from its displacement; $X_{O2}$=the displacement vector–the distance and direction the biasing member 1116 is deformed from its equilibrium length or free length to its loaded length with movement of the first actuator 1108 in the distal direction.

Additionally or alternatively, the restoring force "$F_2$" can also be calculated in terms of the initial restoring force $F_1$, wherein $F_2 = F_1 + (k*X_{12})$, where: $F_1$=the Initial restoring force at initial load length; and $X_{12}$ =a displacement vector–the distance and direction the biasing member 1116 is deformed from its initial length to its loaded length during movement of the first actuator 1108.

When opening (e.g., expanding and extending) the end effector 1106, the first actuator 1108 may be pulled in a proximal direction to withdraw the sheath 1104 and the support members 1158, 1160, and 1162 from the movable members 1152, 1154, and 1156 (FIGS. 9, 10, and 13). In moving the first actuator 1108 in the proximal direction, the first actuator 1108 may engage the plunger 1114 directly by flexible tabs 1120 to withdraw the attached sheath 1104 and the support members 1158, 1160, and 1162 from the movable members 1152, 1154, and 1156. The biasing member 1116 may have little to no influence during the withdrawal, except that the initial restoring force $F_1$ may retain the first actuator 1108 and plunger 1114 a set distance apart by biasing the flexible tabs 1120 against an inner wall of the first actuator 1108.

The end effector 1106 may be in an expanded and extended state when first actuator 1108 has been moved a full stroke in the proximal direction (FIGS. 9, 10, and 13). The front loop of the end effector 1106 can be extended even further to create a larger front loop by pulling the trigger 1118 with the thumb or index finger in the proximal direction to withdraw the sheath 1104 even further and to compress the biasing member 1116 at the same time (FIG. 14). The larger opened front loop may allow stuck stones to be released or enable larger stones to be captured. The restoring force of the compressed biasing member 1116 may return the plunger 1114, sheath 1104, support members 1158, 1160, and 1162, and front loop of the end effector 1106 back to its state prior to actuation of the trigger 1118 when the trigger 1118 is released. The restoring force applied to the plunger 1114 by the biasing member 1116 may be determined by Hooke's law.

When closing the end effector 1116 without a stone present, the first actuator 1108 may be pushed in the distal direction to advance the sheath 1104 and support members 1158, 1160, and 1162 over the movable members 1152, 1154, and 1156 (FIGS. 11 and 15). If the initial restoring force $F_1$ (from the initial compression of the biasing member 1116) is not sufficient to push the sheath 1104 and support members 1158, 1160, and 1162 over the movable members 1152, 1154, and 1156, due to, for example, friction between the sheath 1104 and the drive member 1142 and/or the movable members 1152, 1154, and 1156, and/or between the support members 1158, 1160, and 1162 and the movable members 1152, 1154, and 1156, due to the components traversing a tortuous path, the initial restoring force may be adjusted to a higher magnitude by, for example, replacing the biasing member 1116 with another biasing member having different properties that produce a greater initial restoring force.

To determine an approximate restoring force exerted on the sheath 1104 by the biasing member 1116 (and other biasing members), $F_2$, or the change in load height from $X_1$ to $X_2$ ($X_{12}$), parameters may be measured directly from the handle assembly 1102. More specifically, $X_{12}$ may be the change in the length of the biasing member 1116 from its initial length to its loaded length, and can be measured by the change in plunger length or by the amount of plunger length that is retracted into the first actuator 1108. $X_{12}$ can also be calculated by subtracting the remaining exposed plunger length from its initial exposed plunger length.

The retrieval device 1100 may control the grip force of the front loop of the end effector 1116 as a function of the stone size. The end effector 1106 may operate by reciprocal motion of the sheath 1104 and support members 1158, 1160, and 1162 relative to the drive member 1142 and movable members 1152, 1154, and 1156. The movable members 1152, 1154, and 1156 may be weaved in and out of the support members 1158, 1160, and 1162 to form the end effector 1106 (see FIG. 10). Ends of the movable members 1152, 1154, and 1156 that are not attached to the drive member 1142 may terminate at a coupler (shown but not numbered in FIG. 11), such as the coupler 140. The end effector 1106 may be opened and closed by withdrawing or advancing the sheath 1104 and support members 1158, 1160, and 1162, by the use of the first actuator 1108, relative to the drive member 1142 and movable members 1152, 1154, and 1156. The magnitude of the restoring force that is exerted by the biasing member 1116 may be affected by the size of the stone, and more specifically, the perimeter of the stone that is capture by the front loop of the end effector 1106. Stones of the same perimeter size may generate the same restoring force when captured through movement of the first actuator 1108. A large stone with a large perimeter may generate a restoring force greater than a small stone with a small perimeter when captured, when the first actuator 1108 is actuated.

Referring to FIGS. 13-16, the restoring force of the biasing member 1116 may act on both ends of the biasing member 1116. On one end, the restoring force may be applied directly to the first actuator 1108, while the restoring force at the other end of the biasing member may be applied to the plunger 1114 (and to sheath 1104). The sheath 1104 may branch off to support members 1158, 1160, and 1162, and so may the restoring force. The restoring force may be equally distributed to each of the support members 1158, 1160, and 1162. Put another way, for each of the support members 1158, 1160, and 1162, the force applied may be equal to the restoring force divided by the number of support members. The two movable members within each of the support members 1158, 1160, and 1162 may be subjected to the restoring force acting on support members 1158, 1160, and 1162. The portion of the restoring force distributed to each of the support members 1158, 1160, and 1162 may branch off to the movable members 1152, 1154, and 1156 extending from that support member. For example, when there are two movable members extending from a support member, the force on each movable member may be equal to half of the portion of the restoring force on the support member. A gripping force of the front loop may be the sum of all the forces on the movable members 1152, 1154, and 1156, which may equal the restoring force of the biasing member 1116. The restoring force of the biasing member 1116, at full stroke of the first actuator 1108, may be dependent upon stone size. The maximum grip force that can be applied by the retrieval device 1100 may therefore be dependent on the maximum stone size that can fit into the perimeter of the front loop during a full closing stroke of the first actuator 1108.

Each of the support members 1158, 1160, and 1162 may act as a coupler to hold two of movable members 1152, 1154, and 1156 together to form the front loop. The gripping force of the front loop may be distributed evenly about the front loop when capturing a stone, such that each of the support members 1158, 1160, and 1162 and each of the movable members 1152, 1154, and 1156 may be subjected to the gripping force of the front loop. A minimum tear strength requirement for the support members 1158, 1160, and 1162 should be set above the maximum grip force of the front loop, and/or above the restoring force of the biasing member 1116 when the front loop captures the maximum stone size allowed and the first actuator 1108 undergoes a full closing stroke.

Figure 18:
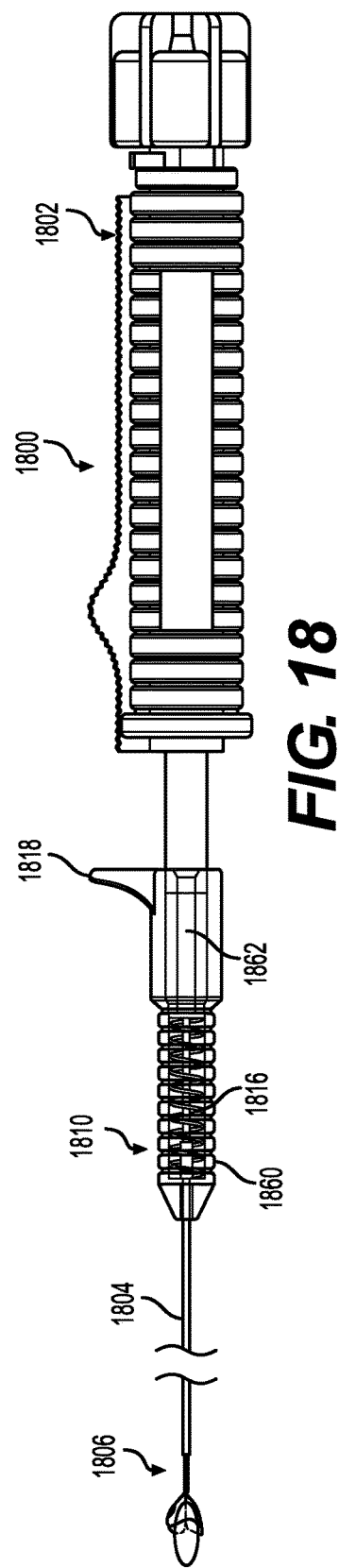
FIG. 18 is a partial cross-sectional side view of a portion of a retrieval device in an extended state, in accordance with aspects of the present disclosure.

FIGS. 18 and 19 show another embodiment of a medical retrieval device 1800 similar to medical retrieval device 1100 in which second actuator in the form of a trigger assembly 1810 is external from and handle assembly 1802. Trigger assembly 1810 may include a biasing member 1816, a biasing member housing 1860 for housing the biasing member 1816 in the form of a spring, a piston body 1862, and a trigger 1818 extending from the biasing member housing 1860. The distal end of the biasing member housing 1860 may be fixed to the outer surface of the sheath 1804 in any suitable manner, such as by glue, heat shrink, etc. In one aspect, the piston body 1862 may include a snap trigger members (not shown) that are recessed in opposing internal slots (not shown) in the biasing member housing 1860. The proximal end of the biasing member housing 1860 may be coupled to a portion of the piston body 1862 in any suitable manner, such as via latches, fasteners, etc. The proximal end of the piston body 1862 may be attached to the distal end of the actuation member 1808 of the handle assembly 1802 in any suitable manner, such as by threads, interference fit, glue etc. Alternatively, the actuation member 1808 and the piston body 1862 may be formed as a single part.

The piston body 1862 may include a distal portion 1866 of a first width or diameter and a proximal portion 1868 of a second width or diameter. The distal portion 1866 slides within a distal reduced opening in the biasing member housing 1860 and the proximal portion 1868 of the piston body 1860 is received in a larger opening of the biasing member housing 1860. The distal portion 1866 of the piston body 1862 includes an end face that abuts a proximal end of biasing member 1816.

The trigger assembly 1810 may be actuated to transition the device from the extended state shown in in FIG. 18 to the further extended state shown in FIG. 19 by moving the trigger 1818 in a proximal direction along piston body 1862 towards the actuation member 1808 to compress the biasing member 1816, in turn withdraw the sheath 1804, and support members. Actuation of the trigger assembly 1810 moves the sheath 1804 an additional distance to further extend or open the end effector 1806 beyond its normal operating range (diameter) for the purposes of capturing a larger target objects through its front opening, releasing a stuck target object, or to enlarge the side opening of the end effector 1806 to allow larger side opening target object capture. Upon release of the trigger 1818, the biasing member 1816 may return the biasing member housing 1860 back to its original stroke length shown in FIG. 18. The change in the length of the biasing member 1816 may be equal to the change in the length of the sheath member 1804 relative to the actuation member 1808. In some embodiments, the biasing member housing 1860 may include relief slots extending therethrough, which may allow portions of the biasing member housing 1860 to expand in various directions. For example, two relief slots may extend along a top portion and two relief slots may extend along a bottom portion of the biasing member housing 1860. The biasing member housing 1860 also may include a flexing tab or ramp portion at a proximal end for engaging a corresponding slot or opening on the piston body 1862 and/or a slot for engaging a ramp.

The disclosed retrieval devices may be utilized in any suitable application involving the capture and removal of materials from the body. Any aspect set forth herein may be used with any other aspect set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

The disclosed devices may be configured to capture fragments having dimensions of about 5 French or smaller. In some arrangements, the disclosed medical devices may be able to capture and release stones having diameters from 1 millimeter to 20 millimeters. In some arrangements, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and the retrieval device may be removed from the human body. In some arrangements, a guide sheath for a ureteroscope may be used to guide the ureteroscope and retrieval device back to a previous position or to a new position to capture additional stones, and protect a ureter wall during stone removal. While moving from the extended and expanded state to the retracted and contracted state, retrieval devices of the present disclosure may ligate larger stones and capture smaller stones within their end effectors.

It will be apparent to those skilled in the art that various modifications and variations can be made in the disclosed systems and processes without departing from the scope of the disclosure. Various aspects of the disclosed devices and processes may be used together in any suitable combination, or used separately. Other aspects of the disclosure will be apparent to those skilled in the art from consideration of the specification and practice of the features disclosed herein. It is intended that the specification and examples be considered as exemplary only.

We claim:

1. A device, comprising:
    a sheath including a distal end and a proximal end;
    an end effector at the distal end of the sheath, the end effector including a plurality of support members fixedly coupled to the distal end of the sheath, and a movable member extending through the support members and movable between an extended state and a retracted state, wherein the support members extend distally beyond a distal end of the sheath in both the extended state and the retracted state;
    a handle assembly at the proximal end of the sheath, the handle assembly including an actuation member operable to move the movable member relative to the support members for transitioning the end effector between the extended state and the retracted state; and
    a biasing member coupled to at least one of the actuation member and the sheath, the biasing member controlling a force exerted by one of the movable member and the support members on the other of the movable member and the support members, the force being generated by relative movement between the movable member and the support members.

2. The device of claim 1, wherein the biasing member is movable between a rest state and a biasing state, the biasing member being compressed or elongated from the rest state to the biasing state.

3. The device of claim 2, wherein the biasing member moves to the biasing state as the end effector transitions to the extended state.

4. The device of claim 2, wherein the biasing member moves from the biasing state to the rest state to transition the end effector to the retracted state with a predetermined force.

5. The device of claim 2, wherein the biasing member moves to the biasing state when the force between the movable member and the support members is outside of a predetermined range.

6. The device of claim 2, wherein movement of the biasing member to the biasing state is caused by relative movement between the actuation member and the sheath.

7. The device of claim 1, wherein the handle assembly includes a handle body slidably coupled to the actuation member.

8. The device of claim 1, wherein the biasing member surrounds at least a portion of the sheath.

9. The device of claim 1, wherein the biasing member has a proximal end fixedly coupled to the sheath, and a distal end movable relative to the sheath.

10. The device of claim 1, wherein the biasing member is fixedly coupled to the actuation member.

11. The device of claim 1, wherein the biasing member has a proximal end fixedly coupled to the sheath, and a distal end fixedly coupled to the sheath.

12. The device of claim 1, wherein the sheath includes at least two sections having different degrees of stiffness, and the biasing member overlaps at least a portion of each of the two sections.

13. The device of claim 1, further including a connector connecting the handle assembly to the proximal end of the sheath, the connector including a port in fluid communication with a lumen of the sheath for injecting a fluid into the lumen of the sheath.

14. The device of claim 1, wherein the end effector is configured to capture an object when transitioned into the extended state, and secure the object when transitioned into the retracted state.

15. The device of claim 14, wherein the biasing member is configured to bias the end effector toward the retracted state.

16. The device of claim 1, further comprising a stroke limiter, and an end cap,
wherein the stroke limiter limits the distal movement of the actuation member, and wherein the end cap is removable to provide access to a proximal end of the movable member.

17. A device, comprising:
a sheath including a distal end and a proximal end;
an end effector at the distal end of the sheath, the end effector including a plurality of support members fixedly coupled to the distal end of the sheath, and a plurality of movable members extending through the plurality of support members, wherein the plurality of movable members are coupled together proximal of the plurality of support members by a coupler;
a handle assembly at the proximal end of the sheath, the handle assembly including an actuation member operable to move the movable members relative to the support members for transitioning the end effector between an extended state and an retracted state; and
a biasing member positioned between the handle body and the actuation member to bias the end effector towards the retracted state with a predetermined biasing force,
wherein movement of the actuation member distally relative to the handle assembly moves the movable members and the coupler distally relative to the sheath and the plurality of support members, and wherein further movement of the actuation member distally relative to the handle assembly moves the movable members distally with the coupler remaining stationary relative to the sheath and the plurality of support members.

18. The device of claim 17, wherein the end effector is configured to capture an object when transitioned into the extended state by a moving force applied to the actuation member.

19. The device of claim 18, wherein the predetermined biasing force closes the end effector around the object with a predetermined closing force when the moving force is released.

20. The device of claim 19, wherein the actuation member is operable to close the end effector around the object with a maximum force that exceeds the predetermined closing force.

* * * * *